(12) United States Patent
Bertelsen et al.

(10) Patent No.: US 8,231,899 B2
(45) Date of Patent: *Jul. 31, 2012

(54) QUICK RELEASE PHARMACEUTICAL COMPOSITIONS OF DRUG SUBSTANCES

(75) Inventors: Poul Egon Bertelsen, Vanløse (DK); Niels Gjørløv Hansen, Fredericksberg (DK); Hermann Ruckendorfer, Reichenthal (AT); Shigeru Itai, Saitama (JP)

(73) Assignee: Nycomed Danmark ApS, Roskilde (DK)

( * ) Notice: Subject to any disclaimer, the term of this patent is extended or adjusted under 35 U.S.C. 154(b) by 865 days.

This patent is subject to a terminal disclaimer.

(21) Appl. No.: 10/758,233

(22) Filed: Jan. 13, 2004

(65) Prior Publication Data

US 2005/0147668 A1    Jul. 7, 2005

Related U.S. Application Data

(63) Continuation of application No. 09/786,864, filed as application No. PCT/DK99/00480 on Sep. 10, 1999, now Pat. No. 6,713,089.

(30) Foreign Application Priority Data

Sep. 10, 1998  (DK) .................................. 1998 01143

(51) Int. Cl.
*A61K 9/20* (2006.01)
*A61K 9/14* (2006.01)

(52) U.S. Cl. ...................................... 424/464; 424/489

(58) Field of Classification Search .................. 424/489, 424/464

See application file for complete search history.

(56) References Cited

U.S. PATENT DOCUMENTS

| | | | |
|---|---|---|---|
| 2,887,439 A * | 5/1959 | Klioze et al. .................. | 424/465 |
| 4,296,128 A * | 10/1981 | Sallmann et al. ............. | 514/540 |
| 5,401,513 A | 3/1995 | Wehling et al. | |
| 5,424,075 A | 6/1995 | Daher et al. | |
| 5,578,316 A * | 11/1996 | Bhardwaj et al. ............. | 424/441 |
| 5,651,988 A * | 7/1997 | Olinger et al. ................ | 424/489 |
| 5,854,226 A * | 12/1998 | Penkler et al. ................. | 514/58 |
| 6,184,220 B1 | 2/2001 | Turck et al. | |
| 6,599,529 B1 * | 7/2003 | Skinhøj et al. ................ | 424/458 |
| 6,682,747 B1 | 1/2004 | Turck et al. | |
| 6,713,089 B1 * | 3/2004 | Bertelsen et al. ............. | 424/489 |

FOREIGN PATENT DOCUMENTS

| | | |
|---|---|---|
| EP | 0 367 056 A2 | 5/1990 |
| EP | 0 553 777 A2 | 8/1993 |
| JP | 2-180814 A | 7/1990 |
| JP | 03-240729 | 10/1991 |
| JP | 03240729 | 10/1991 |
| WO | WO 95/32737 | * 12/1995 |
| WO | WO 96/14839 | 5/1996 |
| WO | WO-99/49845 | 10/1999 |

OTHER PUBLICATIONS

Melia et al., Review article: mechanisms of drug release from tablets and capsules, Aliment. Pharmacol. Therap. (1989) 3, 513-525.*
Remington's Pharmaceutical Sciences, 18$^{th}$ Edition, pp. 1641-1647, 1990.

* cited by examiner

*Primary Examiner* — Robert A Wax
*Assistant Examiner* — Aradhana Sasan
(74) *Attorney, Agent, or Firm* — Edwards Wildman Palmer LLP; Peter F. Corless; Nicholas J. DiCeglie, Jr.

(57) ABSTRACT

The present invention relates to an oral modified release pharmaceutical composition for the administration of a therapeutically and/or prophylactically effective amount of an active substance (a drug substance) to obtain a relatively fast or quick onset of the therapeutic and/or prophylactic effect. The drug substances contained in a modified release pharmaceutical composition according to the invention are suitably a drug substance which has a very low solubility under acidic conditions, i.e. under conditions similar to those present in the stomach and/or drug substances which have a $pK_a$ value below about 5.5 such as in a range of from about 4 to about 5. The composition is based on a powder comprising a therapeutically and/or prophylactically active substance and has such a particle size that: when the powder is subjected to a sieve analysis, then at least about 90% w/w of the particles passes through sieves 180 μm and the powder is contacted with an aqueous medium to form a particulate composition, which has such a particle size that when the particulate composition is subjected to a sieve analysis, then at least about 50% w/w of the particles passes through sieve 180 μm. Furthermore, the composition, when tested in accordance with the dissolution method (I) defined herein employing 0.07 N hydrochloric acid as dissolution medium, releases at least about 50% w/w of the active substance within the first 20 min of the test.

25 Claims, 3 Drawing Sheets

QUICK RELEASE PHARMACEUTICAL COMPOSITIONS OF DRUG SUBSTANCES

The present application is a Continuation of U.S. application Ser. No. 09/786,864, filed on Jul. 10, 2001 (now U.S. Pat. No. 6,713,089 B1, which issued on Mar. 30, 2004), which in turn claimed the prior benefit of International Application PCT/DK99/00480, filed on Sep. 10, 1999.

The present invention relates to an oral modified release pharmaceutical composition for the administration of a therapeutically and/or prophylactically effective amount of an active substance (a drug substance) to obtain a relatively fast or quick onset of the therapeutic and/or prophylactic effect. The drug substances contained in a modified release pharmaceutical composition according to the invention are suitably a drug substance which has a very low solubility under acidic conditions, i.e. under conditions similar to those present in the stomach and/or drug substances which have a $pK_a$ value below about 5.5 such as in a range of from about 4 to about 5. The compositions have been designed in such a manner that two important requirements are obtained, namely i) that the pharmaceutical composition releases the drug substance very fast under acidic conditions whereby the drug substance will become dissolved and, accordingly, available for absorption already almost immediately upon entrance into the stomach, and ii) that the mechanical strength of a composition according to the invention is sufficiently high to withstand normal handling of a pharmaceutical composition and to enable the composition to be coated using traditional coating equipment well known by a person skilled in the art. A composition according to the invention is suitable for use in those cases in which a fast onset of a therapeutic and/or prophylactic effect is desired, e.g. in connection with acute pain or mild to moderate pain. Accordingly, suitable therapeutically and/or propylactically active substances may inter alia be found in the class of drug substances denoted non-steroid anti-inflammatory drug substances (abbreviated in the following: NSAID substances or NSAIDs).

DESCRIPTION OF THE INVENTION

Figure 1:
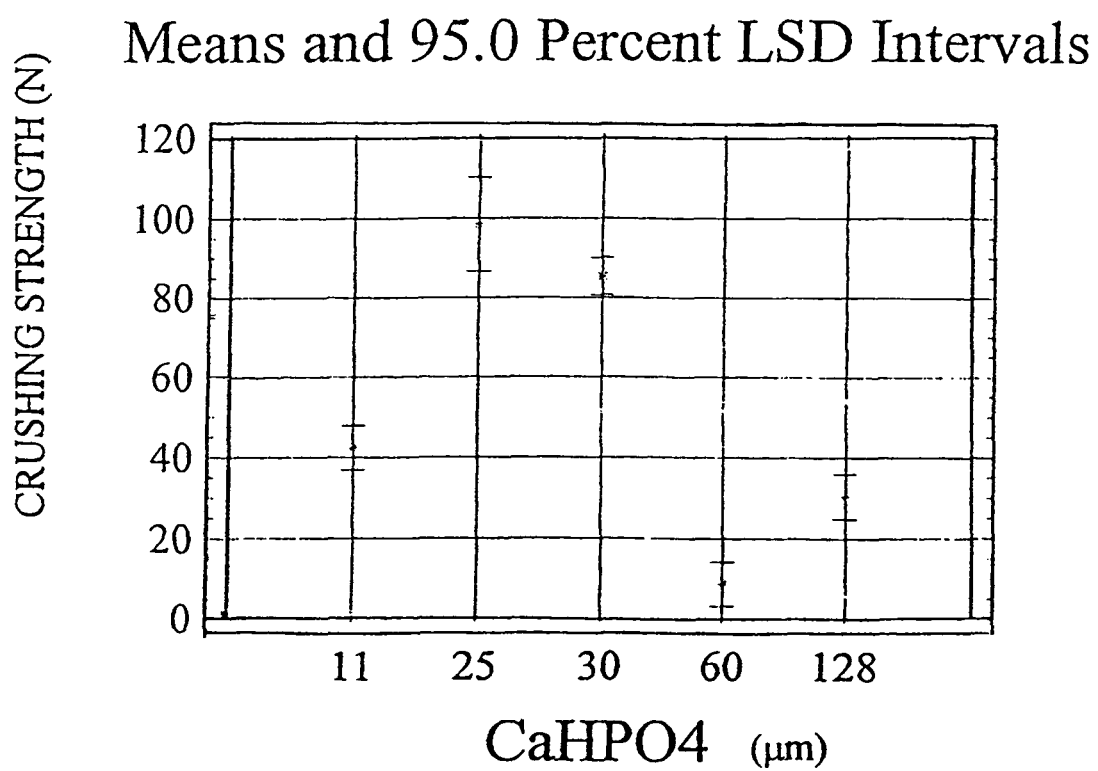
FIG. 1 is a graph of experimental data described in Example 8 indicating that the particle size of calcium hydrogen phosphate has a significant influence on the crushing strength of the tablets.

Pharmaceutical compositions designed to immediate release of a drug substance is known in the art.

Generally, however, the rationale which lies behind the kind of compositions which have been described to enable an immediate release of a drug substance is to employ a traditional formulation approach (such as, e.g., i) plain tablets which have a disintegration time in water of at the most about 30 min, ii) a traditionally formulated granulate or iii) loose powder of the drug substance itself. By doing so the immediate release part of the composition is intended to release the drug substance in a manner which corresponds to a plain tablet formulation or the like and the term "immediate" is in such a context intended to denote that the release of the drug substance is faster than the release from a sustained release composition. The development of the so-called Splash-Dose®, FlashDose® and Flashtabs® are examples of pharmaceutical compositions wherein the focus has been to obtain a very fast disintegration time. Such formulations are suitable for use for drug substances which are readily soluble in the gastrointestinal tract, but basically they do not solve the problems related to drug substances which have poor solubility characteristics.

Especially in those cases where the drug substance has a low solubility in an acidic medium having a pH of from about 1 to about 3, i.e. a pH corresponding to the pH in the stomach, the traditional formulation approach will lead to a pharmaceutical composition which has a suitable fast disintegration time but not necessarily a suitable fast dissolution rate of the drug substance under acidic conditions, i.e. a plain tablet will rapidly disintegrates into granules but the dissolution of the drug substance from the composition and/or the disintegrated composition under acidic conditions may be unsuitable low due to the solubility properties of the drug substance itself. The availability of a drug substance with respect to absorption, i.e. entrance into the circulatory system, is dependant on the presence of the drug substance on dissolved form as it is generally accepted that only dissolved substances are capable of passing the mucous membranes in the gastrointestinal tract. Therefore, it is important that the dissolution of the drug substance is suitably fast even under acidic conditions in order to enable a fast and initial absorption so that a true fast or immediate therapeutic response is obtainable.

For drug substances which are weak acids it is very important to ensure a proper bioavailability of the drug substance already under acid conditions in order to achieve a true rapid therapeutic effect. However, the various approaches disclosed with respect to achievement of a combination of a rapid effect do not seem to take all the above-mentioned factors into account and, hence, there is a need for developing compositions which enable a true rapid onset of the therapeutic effect. To this end, we have especially focused on compositions comprising a drug substance belonging to the class of drug substances normally denoted NSAIDs, but other drug substances having a low solubility in acidic medium and/or a $pK_a$ below about 5.5 may as well be suitable for use in a composition according to the invention.

Moreover, patients suffering from acute pain, mild to moderate pain and/or inflammatory conditions and/or related conditions very often require a dosage and a formulation which enable a fast onset of the therapeutic effect of the NSAID substances. The release from the dosage form must be safe, predictable and reliable. Furthermore, from a technical point of view, the release rate and the release pattern of the active drug substance from the composition should not significantly change during the shelf-life of the composition. A change in the release rate and/or release pattern may have a significant impact on the in vivo performance of the composition.

When testing prior art compositions intended for rapid release of the active drug substance (see e.g. Japanese patent No. 33491/90) the present inventors have revealed problems with respect to the release rate obtained and the robustness of the tablets. Thus, the development of a pharmaceutical composition which is suitable for rapid release of the active substance seems surprisingly to be a balance of on the one hand to obtain a composition which is sufficient robust to withstand normal handling (i.e. to have a sufficient mechanical strength) and on the other hand to enable a fast release and dissolution of the active drug substance in an acidic aqueous medium.

Thus, the purpose of the present invention is to provide a pharmaceutical composition for oral use which is useful for a fast delivery of an active drug substance to the circulatory system upon administration.

In one aspect, the invention relates to a quick release pharmaceutical composition for oral administration comprising a therapeutically and/or prophylactically active substance which has a solubility of at the most about 0.1% w/v in 0.1 N hydrochloric acid at room temperature, the composition being based on a powder comprising the therapeutically and/or prophylactically active substance and having such a particle size that—when the powder is subjected to a sieve analysis—then at least about 90% w/w such as, e.g. at least about 92% w/w, at least about 94% w/w, at least about 95% w/w, at least about 96% w/w, at least about 97% w/w, at least about 97% w/w, at least about 98% w/w or at least about 99% w/w of the particles passes through sieve 180 μm, the powder being contacted with an aqueous medium to form a particulate composition, which has such a particle size that—when the particulate composition is subjected to a sieve analysis—then at least about 50% w/w such as, e.g., at least about 55% w/w. at least about 60% w/w, at least about 65% w/w, at least about 70% w/w, at least about 75% w/w, at least about 80% w/w, at least about 85% w/w, at least about 90% w/w or at least about 95% w/w of the particles passes through sieve 180 μm, and the composition—when tested in accordance with the dissolution method I defined herein employing 0.07 N hydrochloric acid as dissolution medium—releases at least about 50% w/w of the active substance within the first 20 min of the test.

In another aspect the invention relates to a quick release pharmaceutical composition for oral administration comprising a therapeutically and/or prophylactically active substance which has a solubility of at the most 0.1% w/w in 0.1 N hydrochloric acid at room temperature, the composition being in the form of a particulate composition or being based on a particulate composition which is obtained by contacting a powder comprising the therapeutically and/or prophylactically active substance with an aqueous medium in such a manner that the mean particle size of the particles of the particulate composition is at the most about 100% larger than the mean particle size of the powder before contact with the aqueous medium, and the composition—when tested in accordance with the dissolution method I defined herein employing 0.07 N hydrochloric acid as dissolution medium—releases at least about 50% w/w of the active substance within the first 20 min of the test.

In preferred embodiments, the composition releases at least 55% w/w such as, e.g., at least about 60% w/w, at least about 65% w/w, at least about 70% w/w, at least about 75% w/w, at least about 80% w/w, at least about 85% w/w, at least about 90% w/w, at least about 95% w/w, at least about 96% w/w, at least about 97% w/w, at least about 98% w/w or at least about 99% w/w of the total active drug substance present in the composition within the first 20 min of the test.

In another aspect the invention relates to a method for the preparation of a composition according to the invention, the method comprising the steps of i) mixing the therapeutically and/or prophylactically active substance with a) an alkaline substance, b) a filler having binding properties, and, optionally, c) other pharmaceutically acceptable excipients to obtain a powder mixture, ii) contacting the thus obtained powder mixture with an aqueous medium to obtain a wet powder, iii) drying the thus obtained wet powder at a temperature above room temperature until the water content in the powder is at the most about 5% w/w determined as described herein, to obtain a first particulate mixture, iv) sieving the thus obtained first particulate mixture, v) optionally, adding any further pharmaceutically acceptable excipients to obtain a second particulate mixture, vi) optionally, compressing the thus obtained second particulate mixture into tablets, and vii) optionally, coating the thus obtained tablets.

In still further aspects the invention relates to a method for treatment and/or prophylaxis of acute pain and/or mild or moderate pain comprising administering to a patient an effective amount of a therapeutically and/or prophylactically active drug substance in the form a quick release composition according to the invention.

As mentioned above, the solubility of the therapeutically and/or prophylactically active substance in 0.1 N hydrochloric acid at room temperature is at the most about 0.1% w/v such as, e.g., at the most about 0.05% w/v, at the most about 0.01% w/v, at the most about 0.009% w/v, at the most about 0.008% w/v, at the most about 0.007% w/v, at the most about 0.006% w/v, at the most about 0.005% w/v, at the most about 0.004% w/v, at the most about 0.003% w/v, at the most about 0.002% w/v or at the most about 0.001% w/v.

Since the solubility of the therapeutically and/or prophylactically active substance such as, e.g., lornoxicam is <1 mg 1100 ml in 0.1 N HCl (aqueous solution of 0.1 N hydrochloric acid) the present inventors have found that incorporation of e.g. an NSAID substance in free form or in the form of a traditional formulation does not give the desired quick release under acidic conditions to enable a fast onset of the therapeutic effect in vivo.

Furthermore, irrespective of the solubility under acidic conditions, a composition containing an active drug substance which has a very low dissolution rate in 0.1 N or 0.07 N HCl may also present problems with respect to obtaining a quick release and dissolution of the active drug substance. Accordingly, compositions according to the invention may as well contain a therapeutically and/or prophylactically active substance which—when tested by solubility method I described herein—has such a dissolution rate that it allows an amount of at the most 50% w/w of the active substance to be dissolved within the first 20 min of the test.

A quick release of an active drug substance (such as, e.g., an NSAID substance) will, however, take place under acidic conditions provided that the drug substance is presented in a formulation wherein specific means has been used in order to manipulate the release rate so that the release becomes much faster compared to a traditional composition. Thus, the present inventors have found it necessary to adjust the release rate from a traditional composition when the active drug substance either has i) a very low solubility in 0.1 N hydrochloric acid, ii) a very low solubility rate, or iii) has a $pK_a$ below about 5.5 such as, e.g., at the most about 5.3, at the most about 5.2, at the most about 5.0 such as, e.g., in a range of from about 3.4 to about 5.0, in a range of from about 4.0 to about 5.0. Thus, a fast release composition must be manipulated with respect to release in order to achieve a suitable fast release rate.

The present inventors have surprisingly found that in order to obtain a quick release composition containing active drug substances like the ones described above it is necessary to subject the active drug substance to contact with an alkaline substance under certain conditions. Furthermore, the success of the manufacture, i.e. a tablet that fulfils the general requirements of tablets, depends not only on a sole addition of e.g.

sodium hydrogencarbonate (as described in Japanese patent No. 33491/90, Taisho) but also on the following parameters:

1. Contact conditions for the active drug substance and an alkaline substance (contact time, energy input and contact medium)
2. Inclusion of a substance denoted "a filler having binding properties"
3. The mean particle size of the filler having binding properties
4. The mean particle size or the particle size (as obtained from a sieve analysis) of the particulate material obtained after contacting the active drug substance and the alkaline substance with an aqueous medium and before any manufacture of the composition into e.g. tablets
5. The porosity of the particles obtained after contacting the active drug substance and the alkaline substance with an aqueous medium and before any manufacture of the composition into e.g. tablets. The present inventors have found that in certain cases it is possible to obtain suitable release characteristics even if the particle size is not as small as claimed. In those cases, however, the porosity of the particles has been sufficiently high to allow a quick release or alternatively, the hardness of the particles is low.

In the experimental section herein is shown the influence of various process parameters on the properties of the resulting composition. The overall conclusion from the experiments is that in order to obtain a quick release composition it is of utmost importance to control conditions under which the contact between the active drug substance and the alkaline substance takes place. Furthermore, it is demonstrated that in order to obtain a composition with favourable shelf-life it seems necessary that the contact takes place during the manufacturing of the composition (see Example 12 which shows that when the contact between the active drug substance and the alkaline substance has taken place before manufacturing then a decreased shelf-life is obtained). Further investigations have shown that a suitable release is only obtained when the particle size of the particulate material obtained after contact between the active drug substance and the alkaline substance is controlled. (However, as explained above, the particle size requirement can be less stringent if the porosity of the particulate material is increased or if the hardness of the particles is decreased) In other words, it is of utmost importance with respect to the release of the active substance to ensure that the contact in situ between the active drug substance and the alkaline substance takes place under controlled conditions. The contact is performed by adding an aqueous medium to a powder mixture comprising the active drug substance and the alkaline substance and, optionally the filler having binding properties and other pharmaceutically acceptable excipients. The addition of such a medium is performed by the same procedures as if the powder mixture is subjected to a wet granulation process. However, the present inventors have found that the application of the aqueous medium and the process involved must be controlled in such a manner that the resulting particulate mixture is not a traditional granulate, i.e. agglomerates built up of particles of the substances employed. Normally, during a granulation process the particle size is increased by a factor of at least 1.5 and a 200-500% increase may be observed. However, if agglomerates are formed to a major extent, the mean particle size of the particulate mixture will become so large that it has a negative impact on the release rate.

Furthermore, the constitution of the aqueous medium is an important and critical factor (see below).

As a consequence of the above-mentioned formulation requirements, the present inventors have found that the manufacture of a composition according to the invention—even if a wetting step is included—is to be regarded as a process suitable for dry granulation and/or dry compression. It is contemplated that the balance between the qualities of the excipients and the aqueous treatment of the active substance and the alkaline substance is very important in order to obtain a suitable result with respect to both obtaining a quick release and a proper, substantially robust composition. It is believed that a mere effervescent tablet containing e.g. the active substance and sodium hydrogen carbonate will not lead to a controlled quick release because the carbon dioxide formed when such a tablet is dissolved in a glass of water will lead to a quick disintegration but not a quick dissolution. Most likely, the disintegration is so quick that the individual components (e.g. the active substance and the alkaline substance) have no substantial influence on one another. By subjecting the active substance and the alkaline substance to a controlled aqueous treatment, the formation of carbon dioxide during this treatment is believed to take place to some extent but the gas formation is not exhausted. Thus, when the tablet disintegrates in the stomach the remaining carbon dioxide is formed which allows a more ideal disintegration of the tablet and, consequently, gives rise to a local condition in the stomach which is favourable for quick dissolution of the active substance. A local increase in the pH value in the microenvironment of the particles is thus contemplated.

A composition according to the invention may be in the form of a solid composition such as in the form of a particulate composition or in the form of a unit dosage composition such as, e.g., a tablet, a capsule, a sachet or the like.

As mentioned above, the process with respect to the preparation of a composition according to the invention has to be controlled. Thus, it is important that the active drug substance is brought into contact with an alkaline substance. The alkaline substance may be an antacid or an antacid-like substance such as, e.g., sodium hydrogen carbonate, sodium carbonate, potassium carbonate, magnesium carbonate, magnesium hydroxide or magnesium metasilicate aluminate or mixtures thereof. The reaction medium is typically a solvent comprising water and an organic solvent. The organic solvent is a solvent which is miscible with water such as, e.g., a branched or unbranched lower ($C_1$-$C_5$) aliphatic alcohol like, e.g., ethanol, methanol, isopropanol, 1-propanol, 1-butanol, 2-butanol, tert butanol, 1-pentanol, 2-pentanol, 3-pentanol, iso-pentanol and tert. pentanol and mixtures thereof.

The concentration of the organic solvent in the solvent employed is normally from about 0% v/v to about 95% v/v such as, e.g., from about 10% v/v to about 90% v/v, from about 10% v/v to about 80% v/v, from about 15% v/v to about 70% v/v, from about 15% v/v to about 60% v/v, from about 20% v/v to about 50% v/v, from about 20% v/v to about 40% v/v, from about 25% v/v to about 30% v/v such as, e.g. about 25% v/v.

An especially suitable organic solvent is ethanol in a concentration from about 0% v/v to about 95% v/v. The present inventors have found that a contact medium, i.e. an aqueous medium, comprising water and ethanol in a volume ratio of from about 1:50 to about 1:1 is suitable, preferably the ratio is from about 1:10 to about 1:1 such as, e.g. 1:2 or 1:3. Such an aqueous medium may only contain water and ethanol or it may contain other solvents as well.

The contact is generally carried out without any external heating, but of course heating may be employed to speed up the process. The contact performed may result in a formation of a conjugate, an adduct or a salt or a partial salt but investigations are on-going in order to clarify this specific question. Without being limited in any way, it is presently believed that the conjugate or adduct formed may be in the form of a salt or complex formed by a reaction between the therapeutically and/or prophylactically active substance and the alkaline substance employed in process step i) above if the active drug substance and the alkaline substance is processed under conditions where an aqueous contact between the two components does not take place (i.e. under anhydrous conditions) then the present inventors have found that the resulting composition does not fulfil the requirements herein with respect to the release the active drug substance from the composition.

The mean particle size of the antacid-like substance employed in compositions according to the invention (as raw material) is normally at the most about 250 µm, such as at the most about 225 µm, at the most about 200 µm, at the most about 175 µm, at the most about 150 µm, at the most about 145 µm, at the most about 140 µm, at the most about 135 µm, at the most about 130 µm such as, e.g., in a range of from about 20 µm to about 250 µm, in a range of from about 40 µm to about 200 µm, in a range of from about 60 µm to about 175 µm, in a range from about 80 µm to about 150 µm or in a range of from about 100 µm to about 120 µm.

Besides the employment of an alkaline substance in order to enable a suitable contact with the active drug substance, another important ingredient in a composition according to the invention is an ingredient which imparts the necessary mechanical strength to the composition to enable normal handling and, optionally, conventional coating of the composition. In the present context, such an ingredient is denoted "a filler having binding properties". As demonstrated in the Examples herein compositions without such an ingredient or compositions including such an ingredient but having an inappropriate particle size seem to be compositions which are too soft, i.e. have such a poor mechanical strength (friability and crushing strength) that they will not withstand the handling tablets normally have to withstand in order to be used by patients.

Examples of a suitable filler having binding properties for use in compositions according to the invention is, e.g., lactose (such as, e.g., Tabletose®, Pharmatose®), sugar derivatives (such as, e.g., mannitol, sorbitol), calcium carbonate ($CaCO_3$), tricalcium phosphate ($Ca_5(PO_4)_3OH$), calcium hydrogen phosphate ($CaHPO_4$) (such as, e.g., Di-Cafos®, Di-Tab®, Emcompress® or Pharmacompress®), or the like and/or mixtures thereof.

In the experimental section herein calcium hydrogen phosphate has been employed as an example of a filler having binding properties and the results show that the mechanical strength of the tablets prepared is dependent on the particle size of the calcium hydrogen phosphate employed. Too small or too large a particle size will result in tablets which are too soft to withstand normal handling by patients.

Accordingly, the filler having binding properties as raw material has normally a mean particle size of at the most about 140 µm, such as, e.g., at the most about 130 µm, at the most about 120 µm, at the most about 110 µm, at the most about 100 µm, at the most about 90 µm, at the most about 80 µm, at the most about 70 µm, at the most about 60 µm, at the most about 50 µm, at the most about 40 µm, at the most about 35 µm, at the most about 30 µm or at the most about 25 µm such as, e.g., in a range of from about 10 µm to about 80 µm, or in a range of from about 10 to about 65 µm such as e.g. 15-55 µm.

In accordance with the discussion above relating to the particle size, the process step ii) above in a process for the preparation of a composition according to the invention is performed in a conventional high shear mixer employing an energy input which is sufficient to enable a contact to take place between the therapeutically and/or prophylactically active substance and the alkaline substance employed in step i) but at the same time is sufficiently low to avoid formation of a large amount of agglomerates during the mixing.

Thus, in a composition according to the invention, the mean particle size of the particles of the particulate mixture obtained after contact between the active drug substance and the alkaline substance (including any other ingredients present such as, e.g. a filler having binding properties) is at the most about 100% larger than the mean particle size of the powder mixture before the reaction in an aqueous medium. More specifically, the mean particle size of the particle of the particulate composition—is at the most 90% such as, e.g., about 80%, about 75%, about 70%, about 65%, about 60%, about 55% or about 50% larger than the mean particle size of the powder mixture before the reaction in an aqueous medium.

The particle size of the particulate mixture is also expressed by means of results obtained from a sieve analysis, namely that at least about 50% w/w such as, e.g., at least about 55% w/w. at least about 60% w/w, at least about 65% w/w, at least about 70% w/w, at least about 75% w/w, at least about 80% w/w, at least about 85% w/w, at least about 90% w/w or at least about 95% w/w of the particles passes through sieve 180 µm. Before the contact with the aqueous medium, the particle size of the powder is also expressed by means of results obtained from a sieve analysis, namely that at least about 90% w/w such as, e.g. at least about 92% w/w, at least about 94% w/w, at least about 95% w/w, at least about 96% w/w, at least about 97% w/w, at least about 97% w/w, at least about 98% w/w or at least about 99% w/w of the particles passes through sieve 180 µm.

With respect to the mean particle size of the particles of the particulate composition obtained after contact of between the active drug substance with the alkaline substance (including any other ingredients present such as, e.g. a filler having binding properties) it is at the most about 250 µm, such as, e.g. at the most about 240 µm, at the most about 230 µm, at the most about 220 µm, at the most about 210 µm, at the most about 200 µm, at the most about 190 µm, at the most about 180 µm, at the most about 175 µm, at the most about 150 µm, at the most about 125 µm, at the most about 100 µm, at the most about 90 µm, at the most about 80 µm or at the most about 75 µm, whenever appropriate, after a reaction in an aqueous medium.

As mentioned above, a composition according to the invention has such a mechanical strength that it can be subjected to normal handling and coating in conventional coating apparatus without breakage or otherwise rupture. Therefore, a composition according to the invention in the form of tablets having a diameter of 9.5 mm—when subjected to a crushing strength test in accordance with Ph. Eur.—has a crushing strength of at least about 50 N such as, e.g., at least about 60 N, at least about 70 N, at least about 80 N such as, e.g., in a range from about 60 to about 130 N, in a range from about 70 to about 120 N or in a range of from about 75 to about 110 N such as from about 80 to about 100 N. With respect to tablets having other diameters than 9.5 mm, a person skilled in the art will know which crushing strength values become relevant.

An important ingredient with respect to imparting the desired mechanical strength to a composition according to the invention (if the composition is in the form of a tablet) is as mentioned above the filler having binding properties. Therefore, a composition according to the invention—when tested as a composition without the filler having binding properties in the crushing strength apparatus according to Ph. Eur.—is contemplated to have a crushing strength of less than about 45 N such as, e.g., less than about 30 N, less than about 25 N, less than about 20 N, less than about 15 N or less than about 10 N.

In order i) to avoid any substantial degradation of the active drug substance employed in a composition according to the invention and ii) to enable a substantially constant release rate of the active drug substance from a composition according to the invention in the life span of the composition, water content in the composition is at the most about 5% w/w such as, e.g., at the most about 4% w/w, at the most about 3%, at the most about 2% w/w, at the most about 1.5% w/w, at the most about 1.3% w/w, at the most about 1.1% w/w, at the most about 1.0% w/w or at the most about 0.9% w/w determined by a LOD (loss on drying) method (IR dryer, 30 min at 70° C.).

Definitions of Selected Terms Used Herein

The term "modified release composition" used in the present context is defined as a composition from which the release of the drug differs from that of a traditional composition. The release rate is in other words controlled and it is possible to manipulate the release rate by e.g. changing the formulation parameters. The term "modified" is often used in the sense of prolonged, but the term is not restricted to an extended or prolonged effect; the term "modified" may as well cover the situation where the release rate is manipulated in such a manner that a quicker release than normally expected is obtained. Thus, in the present context the terms "quick", "fast" and "enhanced" release as well as "controlled", "delayed", "sustained", "prolonged", "extended" and other synonyms well known to a person skilled in the art are covered by the term "modified", but with respect to the present invention, the term "modified release" is to be understood as a "quick release", "fast release" or "enhanced release".

The term modified release in the present context refers to a composition which can be coated or uncoated and prepared by using pharmaceutically acceptable excipients and/or specific procedures which separately or together are designed to modify the rate or the place at which the active ingredient or ingredients are released (Ph. Eur. 97).

The terms "quick release", "fast release" or "enhanced release" in the present context refer to a modified release composition of which the release of the active ingredient and its subsequent absorption are fast. More specifically, the terms "quick released", "fast release" or "enhanced release" mean that for a composition—when subjected to a dissolution method I described herein—at least about 50% w/w of the active substance is dissolved within the first 20 min of the test.

The term "dosage unit" in the present context refers to one single unit, e.g. a capsule, tablet, a sachet or any other relevant dosage form known within the art. A dosage unit may represent a plurality of individual units which in accordance with the general state of the art may be in the form of a capsule, a tablet, a sachet, etc.

The term "bioavailability" designates the rate and extent to which the drug is absorbed from the modified release composition.

The terms "NSAIDs" or "NSAID substances" are used herein to designate a group of drugs that belongs to non-steroid anti-inflammatory drug substances and pharmaceutically acceptable salts, prodrugs and/or complexes thereof as well as mixtures thereof.

The therapeutic classes mentioned herein are in accordance with the ATC (Anatomical Therapeutic Chemical) classification system.

Active Drug Substances

In the following are given examples of active drug substances which may be incorporated in a composition according to the invention. A majority of the active drug substances mentioned are weak acids, i.e. substances which have a $pK_a$ value below about 5.5 such as, e.g., in a range of from about 3.0 to about 5.5 or in a range of from about 4.0 to about 5.0. In this connection it can be mentioned that the $pK_a$ value for lornoxicam is about 4.7, for naproxen about 4.2, for indometacin about 4.5 and for acetylsalicylic acid about 3.5. Moreover, active drug substances like those mentioned above (i.e. weak acids having a $pK_a$ value of at most about 5.5 or about 5.0) generally have a poor solubility in media having a pH below the $pK_a$ value; as an example the solubility of lornoxicam at a pH corresponding to 0.1 N HCl is less than about 1 mg 100 ml at room temperature and active drug substances like acetylsalicylic acid, indometacin and naproxen are regarded as substances which are practically insoluble in water and 0.1 N HCl at room temperature. From the discussion relating to solubility and availability of the active drug substance in order to get access to the circulatory system it is should be appreciated that the release (dissolution) of the active drug substance from the composition should be quick under acidic conditions, e.g., in 0.1 N HCl even if the active drug substance has a very low solubility in this medium.

Relevant examples of active drug substances suitable for use in compositions according to the invention are in general weakly acidic substances such as, e.g., paracetamol and/or NSAID substances like aminoarylcarboxylic acid derivatives like e. g. enfenamic acid, flufenamic acid, isonixin, meclofenamic acid, mefenamic acid, momiflumate, niflumic acid, and tolfenamic acid, arylacetic acid derivatives like e.g. aceclofenac, acemetacin, amfenac, bromfenac, cimmetacin, diclofenac, etodolac, fentiazac, glucametacin, indomethacin, lonazolac, metiavinic acid, oxametacine, pirazolac, proglumetacin, sulindac, tiaramide, tolmetin, and zomepirac, arylcarboxylic acids like e.g. ketorolac and tinoridine, arylpropionic acid derivatives like e. g. aiminoprofen, bermoprofen, carprofen, dexibuprofen, fenbufen, fenoprofen, flunoxaprofen, flurbiprofen, ibuprofen, ibuproxam, ketoprofen, loxoprofen, naproxen, oxaprozin, pranoprofen, protizinic acid, and tiaprofenic acid, pyrazoles like e.g. epirizole, pyrazolones like e.g. benzpiperylon, mofebutazone, oxyphenbutazone, phenylbutazone, and ramifenazone, salicylic acid derivatives like e.g. acetaminosalol, acetylsalicylic acid, benorylate, eterisalate, fendosal, imidazole salicylate, lysine acetylsalicylate, morpholine salicylate, parsalmide, salamidacetic acid and salsalate, thiazinecarboxamides like a.o. ampiroxicam, droxicam, lornoxicam, meloxicam, piroxicam, and tenoxicam, others like bucillamine, bucolome, bumadizon, diferenpiramide, ditazol, emorfazone, nabumetone, nimesulide, proquazone and piroxicam (e.g. in the form of a betacyclodextrin complex).

From a market point especially the following NSAIDs are interesting: lornoxicam, diclofenac, nimesulide, ibuprofen, piroxicam, piroxicam (betacyclodextrin), naproxen, ketoprofen, tenoxicam, aceclofenac, indometacin, nabumetone, acemetacin, momiflumate, meloxicam, flurbiprofen, tiaprofenic acid, proglumetacin, mefenamic acid, fenbufen, etodolac, tolfenamic acid, sulindac, phenylbutazone, fenoprofen, tolmetin, acetylsalicylic acid, dexibuprofen and pharmaceutically acceptable salts, complexes and/or prodrugs and mixtures thereof.

Other relevant active drug substances are COX-2 (COX is an abbreviation for cyclooxygenase) inhibitors like e.g. celecosib and flosulide.

At present, the most preferred drug substance is lornoxicam and pharmaceutically acceptable salts, complexes and prodrugs thereof. Lornoxicam may be present in a composition according to the invention as the sole drug substance or in combination with other drug substances.

In those cases where a quick release composition of the present invention includes an NSAID substance as the therapeutically active ingredient, the amount of the active drug substance corresponds to from 1 to about 1600 mg of by weight. Alternatively, the dosage form may contain molar equivalent amounts of pharmaceutically acceptable salts thereof. The dosage form contains an appropriate amount to provide a substantially equivalent therapeutic effect.

The active substances mentioned above may be present in a composition according to the invention as i) the only drug substance, or ii) together with at least one other active drug substance such as, e.g. an NSAID substance.

Relevant substances in this context are e.g. antidepressants, opioids, prostaglandine analogs (e.g. misoprostol), glucocorticosteroids, cytostatics (e.g. methotrexate), $H_2$ receptor antagonists (e.g. cimetidine, ranitidine), proton pump inhibitors (e.g. pantoprazole, omeprazole, lansoprazole), antacids, furosemid, acetaminophen (paracetamol), penicillamine, sulfasalazine and/or auranorfin, and—whenever relevant—pharmaceutically acceptable salts, complexes and/or prodrugs and mixtures thereof.

The term "antidepressant" used in the present context includes tricyclic antidepressants as well as other antidepressants and mixtures thereof. Pharmaceutically acceptable salts and/or complexes of antidepressant are also within the definition of antidepressant. Thus, the term "antidepressant" is used here to designate a group of drugs that have, to varying degrees, antidepressive properties and/or suitable properties with respect to alleviation or treatment of neurogenic pain and/or phantom pain. In the present context the term "antidepressant" encompasses drug substances mainly from the therapeutic class N06 or from the following drug classification: Psychoanaleptics excluding anti-obesity preparations; anti-depressants/thymoanaleptics including substances used in the treatment of endogenous and exogenous depression such as, e.g., imipramine, nortriptyline, amitriptyline, oxipramol and MAO-inhibiting substances; lithium; combinations of drugs with ataractics; psychostimulants including drugs which increase the psychic and physical performance and which have a fatigue depressing, stimulating effect such as, e.g., fentyllines, fencamfamine, methylphenidate, amphetamines; pyscholeptic-psychoanaleptic combinations; nootropics [which are a class of psychoactive drugs which are claimed to have a selective action on integrative functions of the CNS. Their action is alleged to be particularly associated with intellectual function, learning and memory. Nootropics include preparations containing substances such as piracetam, pyritinol, pyrisuccideanol maleate, meclofenoxate, cyprodenate and their combinations with other substances, excluding those products with a vasodilatory action (see the therapeutic class C04A). Combinations with cardiac glycosides are classified in the therapeutic class C01A]; and neurotonics and other miscellaneous products including products which are not classified above such as single or combination products containing bisibutiamin, deanol and derivatives, GABA, GABOB, N-acetyl asparaginic acid glutaminic acid and salts, kavain, phospholipid, succinodinitrate.

The presently most interesting drug substances belong to the tricyclic antidepressants. Relevant examples of antidepressants are: tricyclic antidepressants such as, e.g. dibenzazepine derivatives like carpipramine, clomipramine, desipramine, imipramine, imipraminoxide, imipramine pamoate, lofepramine, metapramine, opipramol, quinupramine, trimipramine; dibenzocycloheptene derivatives like amitriptyline, amitriptyline and chlordiazepoxide, amitriptyline and medazepam, amitriptyline and pridinol, amitriptyline and perphenazine, amitriptylinoxide, butriptyline, cyclobenzaprine, demexiptiline, nortriptyline, nortriptyline and diazepam, nortriptyline and perphenazine, nortriptyline and fluphenazine, nortriptyline and flupentixol, noxiptilin, protriptyline; dibenzoxepine derivatives like doxepin; and other tricyclic anti-depressants like adinazolam, amoxapine, dibenzepin, dimetacrine, dosulepin, dosulepin and diazepam, dothiepin, fluacizine (fluoracyzine, toracizin), iprindole, maprotiline, melitracen, melitracene and flupentixol, pizotyline, propizepine, and tianeptine; other anUdepressants like 5-hydroxytryptophan, ademetionine, amfebutamone, amfebutamone hydrochloride, amineptine, amineptine hydrochloride, amisulpride, fluoxetine hydrochloride, fluoxetine, hypericin, lithium carbonate, sertraline hydrochloride, sertraline, St John's wort dry extract, trimipramine maleate, citalopram, citalopram hydrobromide, clomipramine chloride, clomipramine hydrochloride, d-phenylalanine, demexiptiline, demexiptiline hydrochloride, dimethacrine tartrate, dothiepin, dothiepin hydrochloride, doxepin, fluphenazine hydrochloride, fluvoxamine, fluvoxamine hydrogen maleate, fluvoxamine maleate, ginkgo biloba, indalpine, isocarboxazide, johanniskrauttrockenestrakt, 1-tryptophan, lithium citrate, lithium sulfate, lofepramine, maprotiline, maprotiline hydrochloride, maprotilin mesilate, medifoxamine, metaprimine fumarate, mianserin, moclobemide, nitroxazepin hydrochloride, nomifensine, nomifensine maleate, nomifensin hydrogenmaleat, oxitriptan, paroxetine, paraoxetine hydrochloride, phenetzine, phenelzine sulfate, piracetam, pirlindole, pivagabine, prolintane hydrochloride, propizepine hydrochloride, protriptyline hydrochloride, quinupramine, remoxipride hydrochloride, rubidium chloride, setiptiline maleate, tianeptine sodium, trazodone hydrochloride, venlafaxine hydrochloride, maprotiline, toloxatone, tranylcypromine, trazodone, trazodone hydrochloride, viloxazine, viloxazine hydrochloride, zimelidine, zimelidine dihydrochloride.

At present, the most interesting antidepressant drug substances for use in a composition according to the invention are amitriptyline and/or imipramine and pharmaceutically acceptable salts, complexes and prodrugs thereof. Amitriptyline and/or imipramine may be present in a composition according to the present invention either as the sole drug substance or in combination with other drug substances. Amitriptyline is a very interesting drug candidate with respect to preventing and/or treating neurogenic pains and phantom pains.

The term "opioid" is used here to designate a group of drugs that are, to varying degrees, opium- or morphine-like in their properties. The term includes natural and synthetic opioids as well as active metabolites such as morphine-6-glucuronide and morphine-3-glucuronide, and mixtures of opioids. Pharmaceutically acceptable salts and/or complexes of opioids are also within the definition of opioids.

Further relevant examples of opioids for us in compositions according to the invention include alfentanil, allylprodine, alphaprodine, anileridine, benzylmorphine, bezitramide, buprenorphine butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocondone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, myrophine, nalbuphine, narceine, nicormorphine, norlevorphanol, nornethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, salts thereof, mixtures of any of the foregoing, mixed µ-agonists/antagonists, µ- and/or κ-agonists, combinations of the above, and the like.

Within the scope of the invention is of course that more than one active drug substance may be present in a composition, e.g. more than one NSAID substance and/or drug substances within the same or different therapeutic classes. Specific relevant therapeutic classes are M01A (NSAIDs), R05D, N02 (analgesics), N2A (opioids) and N2B (non-narcotic analgesics).

Dosage

In general, the dosage of the active drug substance present in a composition according to the invention depends inter alia on the specific drug substance, the age and condition of the patient and of the disease to be treated.

Compositions according to the invention will generally contain an amount of the active drug substance which enables a sufficient therapeutic and/or prophylactic response.

In order to illustrate the broad ranges of suitable doses, the recommended daily doses for selected NSAID substances is listed in the following:

Aceclofenac: 200 mg
Diclofenac: 100 mg
Etodolac: 400 mg
Fenbufen: 900 mg
Fenoprofen: 1.5 g
Flurbiprofen: 200 mg
Ibuprofen: 1.6 g
Indometacin: 100 mg
Ketoprofen: 200 mg
Meloxicam: 15 mg
Nabumeton: 1 g
Naproxen: 750 mg
Piroxicam: 20 mg
Sulindac: 300 mg
Tenoxicam: 20 mg
Tiaprofenic acid: 600 mg
Tolfenamic acid: 400 mg
Tolmelin: 800 mg The amount of e.g. an NSAID substance in a quick release composition according to the invention may be selected so that is corresponds to about 1 mg, 2 mg, 3 mg, 4 mg, 5 mg, 8 mg, 10 mg, 12 mg, 16 mg, 20 mg, 24 mg, 25 mg, 30 mg, 32 mg, 50 mg, 60 mg, 100 mg, 200 mg, 300 mg, 400 mg, 500 mg, 600 mg, 700 mg, 800 mg, 900 mg, 1 g, 1.1 g, 1.2 g, 1.3 g or 1.6 g of NSAID substance which are dosages generally known in the art.

A composition according to the invention may be produced in different series of dosage forms of e.g. 4 mg, 8 mg, 12 mg, 16 mg, 24 mg, 32 mg etc., each of the series having individual properties resulting from the design of modified release of the composition. Any desired total dosage can then be selected from the relevant dosage forms within each of the series.

The preferred dosage form according to the invention is in the form of a capsule, tablet, sachet etc. The size of the dosage form is adapted to the amount of the active drug substance contained in the composition.

The above suggested dosage amounts should not be regarded as a limitation of the scope of the invention as it is obvious for the skilled person that any desired amount of the active drug substance may be applied and is only limited by the size of the composition and the type of the active drug substance.

Pharmaceutically Acceptable Excipients

Apart from the active drug substance in the composition, a pharmaceutical composition according to the invention may further comprise pharmaceutically acceptable excipients.

In the present context, the term "pharmaceutically acceptable excipient" is intended to denote any material which is inert in the sense that it substantially does not have any therapeutic and/or prophylactic effect per se. A pharmaceutically acceptable excipient may be added to the active drug substance with the purpose of making it possible to obtain a pharmaceutical formulation which has acceptable technical properties. Although a pharmaceutically acceptable excipient may have some influence on the release of the active drug substance, materials useful for obtaining modified release are not included in this definition.

Fillers/diluents/binders may be incorporated such as sucrose, sorbitol, mannitol, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivaceli, Ming Tai® and Solka-Floc®), hydroxypropylcellulose, L-hydroxypropylcellulose (low-substituted) (e.g. L-HPC-CH31, L-HPC-LH11, LH 22, LH 21, LH20, LH32, LH31, LH30), dextrins, maltodextrins (e.g. Lodex® 5 and Lodex® 10), starches or modified starches (including potato starch, maize starch and rice starch), sodium chloride, sodium phosphate, calcium phosphate (e.g. basic calcium phosphate, calcium hydrogen phosphate), calcium sulfate, calcium carbonate. In pharmaceutical formulations according to the present invention, especially microcrystalline cellulose, L-hydroxypropylcellulose, dextrins, maltodextrins, starches and modified starches have proved to be well suited.

Disintegrants may be used such as cellulose derivatives, including microcrystalline cellulose, low-substituted hydroxypropyl cellulose (e.g. LH22, LH21, LH20, LH32, LH31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®D).

Glidants and lubricants may be incorporated such as stearic acid, metallic stearates, talc, waxes and glycerides with high melting temperatures, colloidal silica, sodium stearyl fumarate, polyethylenglycols and alkyl sulphates.

Surfactants may be employed such as non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate) and cationic (e.g., benzalkonium chloride, benzethonium chloride and cetrimide) or mixtures thereof.

Other appropriate pharmaceutically acceptable excipients may include colorants, flavouring agents, and buffering agents.

A coating may also be applied on a composition according to the invention provided that the coating does not substantially retard the release of the active drug substance from the composition. Typically, a film coating may be employed.

Manufacturing Processes

As discussed above, the invention also relates to a method for preparing a composition according to the invention. The method comprising the steps of i) mixing the therapeutically and/or prophylactically active substance with a) an alkaline substance, b) a filler having binding properties, and, optionally, c) other pharmaceutically acceptable excipients to obtain a powder mixture, ii) contacting the thus obtained powder mixture with an aqueous medium to obtain a wet powder, iii) drying the thus obtained wet powder at a temperature above room temperature until the water content in the powder is at the most about 5% w/w determined as described herein, to obtain a first particulate mixture, iv) sieving the thus obtained first particulate mixture, v) optionally, adding any further pharmaceutically acceptable excipients to obtain a second particulate mixture, vi) optionally, compressing the thus obtained second particulate mixture into tablets, and vii) optionally, coating the thus obtained tablets.

The individual steps of the method are performed in apparatus which are suitable for the specific type of process step. It is of course advantageous to performed more than one step in the same apparatus provided that the critical conditions can be controlled in the desired manner.

With respect to step i), the most critical parameter is the particle size of the starting material, cf. the discussion above, especially the particle size of the filler having binding properties.

Step ii) is a very important step and the conditions under which this step is carried out are very critical. Most important is it that in this step the powder is subjected to not a granulation process but a wetting process resulting in a particulate material in which the individual particles of the powder mixture are brought into contact and held together by binding forces which are established by the energy input given during step ii) The present inventors have made investigations which show that A) if a normal granulation process is employed, i.e. a process which results in the formation of agglomerates, or B) if a direct compression (see Example 20b) procedure is employed, i.e. a process in which step ii) is irrelevant because no wetting of the powder blend takes place, then the final composition does not fulfil the requirements with respect to quick release. However, as reported in the experimental section herein the use of the correct conditions may lead to a composition from which almost 100% w/w of the active substance (at least 90-95% w/w) is released in vitro within the first 10 min of the test employing Dissolution method I as described below.

The mechanism which is believed to take place in step ii) is to bring the active substance and the alkaline substance in close contact and at the same time utilise conditions which are favourable with respect to building up a composition which has optimal disintegration and dissolution properties. To this end, it is believed that employment of an alkaline substance which is able to produce gas, carbon dioxide, upon contact with water (or an aqueous medium having a pH below 7) is acceptable as a certain production of gas during the wetting procedure facilitates the necessary controlled disintegration of the final compostion, i.e. avoiding a too fast disintegration due to an excessive amount of gas production when the final composition disintegrates. To this end, the inventors have performed experiments in which the active substance and the alkaline substance have been subjected to a treatment with an aqueous medium and subsequently dried and then the particulate material obtained in this manner has been employed in step i) of the method described above. However, this procedure does not lead to a satisfactory result and the composition obtained has a unacceptable shelf-life, i.e. the aqueous pre-treatment of the active substance with the alkaline substance seems to have a negative influence on the chemical stability of the active substance itself.

The critical parameters in step ii) are the contact medium, the contact time and the energy input (i.e. the energy added to the powder mixture to build up the particulate material). The particle size of the resulting particulate material is a very important parameter, cf. the discussion above, but as mentioned above it is possible successfully to obtain suitable composition even if the particle size of the particulate material is larger than the sizes claimed if the particles either are soft or have an increased porosity.

The contact medium is not used as a granulation medium, e.g. no water-soluble binders is present in the medium. Typically the medium is an aqueous medium having a composition as described hereinbefore. A preferred medium is a medium containing ethanol and water and wherein the concentration of ethanol in the solvent is from about 0% v/v to about 95% v/v such as, e.g., from about 10% v/v to about 90% v/v, from about 10% v/v to about 80% v/v, from about 15% v/v to about 70% v/v, from about 15% v/v to about 60% v/v, from about 20% v/v to about 50% v/v, from about 20% v/v to about 40% v/v, from about 25% v/v to about 35% v/v such as, e.g. about 33.3% v/v. An especially suitable aqueous medium is a medium containing ethanol and water in a volume ratio of from about 1:10 to about 1:1 such as from about 1:3 to about 1:1.5, e.g. 1:2.

With respect to the energy supply during step ii) the present inventors have found that the use of a mixer of the type high speed impeller is suitable.

The energy supplied during step ii) may advantageously be added discontinuous, i.e. with intervals of wet-massing and wet-resting (i.e. intervals in which the aqueous medium is added to the powder during mixing and intervals in which no adding of aqueous medium takes place and no mixing takes place as exemplified in Example 16).

As a starting point of determining the necessary energy supply when either changing the batch size or the apparatus, the swept volume is a guidance.

The swept volume is related to the energy input and is defined in the following way:

The vertical swept volume out by one impeller blade at each revolution is calculated by dividing the blade area into vertical segments. Based on this volume and the impeller speed, the volume swept out by the blades per second is determined relative to the volume of the product or the volume of the bowl.

Moreover, it is important that step ii) is performed in a suitable apparatus which enables an energy input which a) is sufficient to bringing the particles in contact with the aqueous medium without substantially deteriorate the stability of the final composition and/or b) is sufficient to bringing the therapeutically and/or prophylactically active substance and the alkaline substance in contact with the aqueous medium without negatively influencing the release rate of the active substance from the final composition.

As discussed above, step ii) is typically performed in a conventional high shear mixer employing an energy input which is sufficient to enable a contact to take place between the therapeutically and/or prophylactically active substance and the alkaline substance employed in step i) but at the same time is sufficiently low to avoid formation of a large amount of agglomerates during the mixing.

The mean particle size of the particles of the first particulate mixture is at the most about 100% larger than the mean particle size of the powder mixture from step i) before subjecting the powder mixture to the reaction in the aqueous medium employed in step ii).

More specifically, the mean particle size of the particle of the first particulate mixture is at the most about 90% such as, e.g., about 80%, about 75%, about 70%, about 65%, about 60%, about 55% or about 50% larger than the mean particle size of the powder mixture from step i) before subjecting the powder mixture to the reaction in an aqueous medium employed in step ii).

The particle size is also expressed by results of a sieve analysis and then the following sizes are relevant:

The powder obtained in step i) has such a particle size that—when the powder is subjected to a sieve analysis—then at least about 90% w/w such as, e.g. at least about 92% w/w, at least about 94% w/w, at least about 95% w/w, at least about 96% w/w, at least about 97% w/w, at least about 97% w/w, at least about 98% w/w or at least about 99% w/w of the particles passes through sieve 180 μm, and the first particulate mixture obtained in step iii) has such a particle size that—when the particulate composition is subjected to a sieve analysis—then at least about 50% w/w such as, e.g., at least about 55% w/w, at least about 60% w/w, at least about 65% w/w, at least about 70% w/w, at least about 75% w/w, at least about 80% w/w, at least about 85% w/w, at least about 90% w/w or at least about 95% w/w of the particles passes through sieve 180 μm.

Typically, the mean particle size of the particles of the first particulate mixture is at the most about 250 μm, such as, e.g. at the most about 240 μm, at the most about 230 μm, at the most about 220 μm, at the most about 210 μm, at the most about 200 μm, at the most about 190 μm, at the most about 180 μm, at the most about 175 μm, at the most about 150 μm, at the most about 125 μm, at the most about 100 μm, at the most about 90 μm, at the most about 80 μm or at the most about 75 μm.

Step iii) in which the wet particulate material is dried is of course also important in order to obtain a proper shelf-life of the product. The remaining steps are steps well known in the art of pharmaceutical formulation and a person skilled in the art knows hand-books in which further details are found.

In the following examples, the invention is further disclosed.

Materials and Methods

Materials employed in the compositions which were investigated in the course of development of the present invention were as given in the following. In those cases where reference is given to an official pharmacopoeia, the reference is to the current edition of the stated pharmacopoeia.

The following abbreviations are used:

Ph. Eur.: European Pharmacopoeia

USP/NF: United States Pharmacopoeia National Formulary

DLS: Dansk Laegemiddelstandard

| Materials | Quality | Manufacturer |
| --- | --- | --- |
| Cellulosum microcristallinum (Avicel PH 101) | Ph. Eur. | FMC |
| Dibasic Calcium Phosphate, Anhydrous (Calcium hydrogen phosphate) | USPNF | Kyowa |
| Sodium bicarbonate | USPNF | Kirsch |
| Hydroxypropylcellulose (HPC L fine) | Ph. Eur. | Nippon Soda |
| Low-substituted Hydroxy Propyl Cellulose | USPNF | Shin-Etsu |
| Calcium stearate | Ph. Eur. | Akcros Chemicals |
| Ethanol, 96% | DLS | Danisco |
| Aqua Purificata | Ph. Eur. | |
| Macrogol 6000 (polyethylene glycol) | Ph. Eur. | BASF |
| Hydroxypropylmethylcellulose (Pharmacoat 603) | USP | Shin-Etsu |
| Hydroxypropylmethylcellulose (Pharmacoat 606W) | USP | Shin-Etsu |
| Magnesium stearate | Ph. Eur. | Ackros |
| Polyplasdone XL | USPNF | ISP |
| Aerosil 200 | Ph. Eur. | Degussa |
| Talc | Ph. Eur. | Luzenac val chisone |
| Titanium dioxide | Ph. Eur. | Bayer |
| Hydroxypropylmethylcellulose 5 | Ph. Eur. | Dow |
| Propylene glycol | Ph. Eur. | Arcochemie |
| Ibuprofen | Ph. Eur. | Albemarle S.A. |
| Furosemide | Ph. Eur. | Assia Chemical Industries Ltd. |
| Sodium lauryl sulfate | | Henkel |
| Lornoxicam | | Nycomed |

Dissolution Method I 0.07 N HCl (lornoxicam)

Lornoxicam has a very low solubility under acidic conditions such as in 0.1 or 0.07 N HCl. Inter alia in order to show that the relatively fast release fraction indeed releases lornoxicam at acidic pH (simulating the pH conditions in the stomach), dissolution method I is employed.

Test Method

Apparatus: Ph. Eur. Dissolution test for solid dosage forms and USP XXIII <711> apparatus 2, equipped with Sotax AT7 and Perkin Elmer UV/VIS Spectrometer Lambda 2. The measurement was performed continuously using Perkin-Elmer Dissolution Software for Lambda Series UVNIS Spectrometers Version 3.0/JAN 94. The calculations were performed using the same software.

Glass fibre filter: Whatman GF/F

Dissolution medium: 900.0 ml dissolution medium (see below)

Number of revolutions: 100 rpm

Stirrer: Paddle

Temperature of dissolution medium: 37° C.±0.5° C.

Measuring times: every five minutes and 20 min after the start of the test (details appear from the following examples)

Analysis Method

Detection wavelength: $\lambda=378$ nm

Measuring equipment: UV/VIS—spectrophotometer, 1 cm cuvette

Preparation of Reagents

Dissolution medium: Weigh out 50.0 g of sodium chloride and measure out 141.6 ml of concentrated hydrochloric acid. Dissolve the chemicals in distilled water and dilute to 25 l with distilled water.

Standards

Stock solutions: 2 stock solutions ($S_1$ and $S_2$) with a concentration of 200 μg/ml lornoxicam were prepared. Lornoxicam is dissolved in solvent for standards (cf. below).

Standards: 20.00 ml of each of the stock solutions is added to the reference vessel (cf. below).

Solvent for standards: 1.5% w/w aqueous sodium acetate solution: methanol (1:1)

Test Procedure 900 ml of dissolution medium is filled to each of the vessels (typically three or six vessels for the product and one vessel for reference solution). The medium is heated to 37° C.±0.5° C. The product to be tested (e.g. a therapeutically and/or prophylactically active substance, a particulate composition, a granulate, granules or a composition in the form of a tablet, capsule or a sachet) is placed in the vessel. In the last vessel, 20.0 ml of each of the stock solutions are added. The spindle is started, and the absorbance of the samples and standards is measured at 378 nm with zero setting towards the dissolution medium.

The percentage dissolved is measured over a suitable time interval.

Calculation for Dissolution Method

Percentage dissolved was calculated with reference to an external standard in the reference vessel.

The concentration of the standard in the reference vessel is calculated by the formula below:

$$\text{mg lornoxicam per 1000 ml} = \left(\frac{q_1 \cdot 20}{V} + \frac{q_2 \cdot 20}{V}\right) \cdot \frac{1000}{940}$$

Where:
$q_1$=amount of standard weighed out for $S_1$ (mg)
$q_2$=amount of standard weighed out for $S_2$ (mg)
20=added volume of $S_1$ and $S_2$ to the reference vessel (ml)
V=dilution volume of the standard (ml)
940=volume in the reference vessel after addition of the standards ($S_1$ and $S_2$) to the vessel (ml)
1000=conversion factor to 1000 ml The content of lornoxicam as percentage dissolved was calculated from the formula below:

$$\frac{abs_{sample} \cdot StA \cdot 900 \cdot x \cdot 100}{abs_{StA} 1000 \cdot q_{tablet} \cdot 8} \cdot \frac{n}{100}$$

Where
$abs_{sample}$=absorbance measured in each vessel containing samples
StA=mg lornoxicam pr 1000 ml in the vessel containing standard
900=volume of the medium (ml)
100=factor converting to percent
$abs_{StA}$=absorbance measured in vessel containing the standard
1000=factor converting the concentration of the standard to mg/ml
8=declared content (mg) in the tablet
n=potency of the standard (%)
100=factor converting to percent Determination of Dissolution Rate—Solubility Method I The dissolution rate of an active substance is determined using the same procedure as described under "Dissolution method I" above and with any relevant modification in the calculation method described.

Test for Resistance to Crushing of Tablets

The test is performed in accordance with the guidelines given in Ph. Eur. 1997, pp 135-136.

The following examples are intended to illustrate specific embodiments of the present inventions but are not intended in any way to limit the invention.

EXAMPLE 1

Investigation of the Influence of Various Process Parameters on the Dissolution Rate of the Final Composition Initial investigations by the inventors have indicated that the dissolution rate of a therapeutically and/or prophylactically active substance seems to be dependant on the manufacturing process employed. Especially, it was judged necessary to control critical parameters like e.g. i) spray pressure during the addition of reaction medium, ii) reaction time, iii) amount of reaction medium added and iv) the mixing intensity (i.e. ±employment of a chopper). Accordingly, labtrials based on a $2^4$ factorial design with replication of centre points were performed.

The purpose of the trials was to investigate the influence of certain process parameters on the dissolution of the therapeutically and/or propylactically active substance from the composition obtained. The dissolution test was performed in 0.07 N hydrochloric acid employing the dissolution method I described herein and the amount of active substance released and dissolved after 20 min of the dissolution test was determined.

The factors and the levels investigated are listed below:

| Factors | Lower level | High level |
|---|---|---|
| Spray pressure[a] | 0.5 bar | 2.0 bar |
| Reaction time[b] | 2 min | 9 min |
| Amount of medium | 1440 g | 1640 g |
| Intensity of mixing (+/− employment of chopper) | − | +[c] |

[a] the spray pressure was measured just before the inlet of air to the nozzle
[b] excl. time for distribution of the water
[c] the speed of the chopper was 1

The design included 20 trials as the centrepoints (with (+) or without (−) chopper) were replicated once. The composition employed throughout the trials is described in the following together with the manufacturing process employed for trial 1 (batch No. 30069733). The manufacturing process for the other trials was in accordance with trial 1 apart from the modifications which were necessary in order to test the above-mentioned process parameters (see Table 1 below).

| | | |
|---|---|---|
| I | Lornoxicam | 80.0 g |
| II | Sodium hydrogen carbonate | 400.0 g |
| III | Avicel PH 101 | 960.0 g |
| IV | Calcium hydrogen phosphate anhydrous | 1104.0 g |
| V | L-HPC | 480.0 g |
| VI | Hydroxy propyl cellulose | 160.0 g |
| VII | Purified water | 1230.0 g |
| VIII | Ethanol 99.9% | 410.0 g |
| IX | Calcium Stearate | 5.0 g* |

*amount adjusted for a total of 1 kg of I-VI.

II-VI were admixed for 6 min in a Fielder intensive mixer with impeller speed I and without use of chopper. Then a 1 kg aliquot was mixed with I in a planetary mixer for 10 min. The mixture was sieved through a 0.5 mm sieve and then admixed in the Fielder to the remaining II-VI mixture.

VII+VIII were mixed and applied to the mixture (I–VI) by a 2 components nozzle with a spray pressure of 0.5 bar and with a spraying time of approx. 2 min. The impeller speed was I and the chopper speed I. When spraying was completed, the mixing was continued for 9 min at impeller speed I and chopper speed I.

The drying of the wet mixture was carried out in a Aeromatic fluid bed with an inlet air temp of 65° C. The drying was continued for 45 min. Thereafter, the mixture was sieved through a 1.0 mm sieve and the drying process was continued with an inlet air temperature of 80° C. When the outlet temperature reached 50° C., after approx. 20 min, the drying was stopped.

1200 g of the thus obtained particulate mixture were sieved through a 0.7 mm sieve. IX was sieved through a 0.3 mm sieve and admixed to 1000 g of the sieved particulate mixture in a planetary mixer for 10 min.

The thus obtained particulate mixture was compressed by a Korsch rotary tabletting machine. Punches: 9.5 mm. A compound cup was used. Weight of the tablet: 320 mg.

Process parameters employed and dissolution rates obtained from compositions corresponding to trials 1-20 are shown in the following Table 1.

after 20 min of the dissolution test employing dissolution method I described herein).

Statistical analysis showed that the following process parameters were significant or almost significant at the 5% level with respect to influence on the dissolution rate.

Spray pressure (P=0.03)

Amount of medium (P=0.06)

Interactions between spray pressure and amount of medium (P=0.02)

Interactions between spray pressure and chopper (P=0.03)

Interactions between amount of medium and reaction time (P=0.002)

Interactions between spray pressure, reaction time and amount of medium (P=0.04)

TABLE 1

$2^4$ factorial design with replication of centre point

| Batch No. | Trial No. | Pressure (bar) | Time (min) | Amount (g) | Chopper yes/no | Release 20 min % |
|---|---|---|---|---|---|---|
| 30069733 | 1 | 0.5 | 9 | 1640 | yes | 91.85 |
| 1079732 | 2 | 2 | 2 | 1440 | yes | 89.88 |
| 2079732 | 3 | 0.5 | 9 | 1640 | no | 90.85 |
| 2079734 | 4 | 0.5 | 2 | 1440 | yes | 92.83 |
| 3079732 | 5 | 1.25 | 5.5 | 1540 | yes | 94.14 |
| 7079732 | 6 | 2 | 9 | 1640 | yes | 79.64 |
| 8079732 | 7 | 2 | 9 | 1640 | no | 84.17 |
| 8079734 | 8 | 2 | 2 | 1640 | yes | 88.14 |
| 9079732 | 9 | 0.5 | 9 | 1440 | no | 91.24 |
| 10079732 | 10 | 2 | 9 | 1440 | yes | 93.76 |
| 11079732 | 11 | 2 | 9 | 1440 | no | 95.8 |
| 14079732 | 12 | 2 | 2 | 1640 | no | 93.77 |
| 1479735 | 13 | 2 | 2 | 1440 | no | 89.49 |
| 15079732 | 14 | 1.25 | 5.5 | 1540 | no | 94.03 |
| 15079734 | 15 | 1.25 | 5.5 | 1540 | no | 92.07 |
| 16079732 | 16 | 0.5 | 2 | 1440 | no | 88.99 |
| 21079732 | 17 | 0.5 | 9 | 1440 | yes | 95.23 |
| 21079734 | 18 | 0.5 | 2 | 1640 | no | 93.93 |
| 22079732 | 19 | 1.25 | 5.5 | 1540 | yes | 94.54 |
| 22079734 | 20 | 0.5 | 2 | 1640 | yes | 94.25 |

In general the following technical properties of the tablets were obtained (uncoated cores):

Water content (LOD—30 min at 70° C.): 1.4-2.2%

Disintegration time (mean): 3-6 min.

Tablet hardness (crushing strength) (mean): 80-100 N

Uniformity of the mass ($S_{rel}$): 1-2%

Conclusion

As shown in Table 1 above, the dissolution of lornoxicam from the various compositions tested varies from 79% w/w to about 94% w/w (the amount dissolved has been determined

EXAMPLE 2

Design of Lornoxicam Compositions having a Quick Release of Lornoxicam in 0.07 N Hydrochloric Acid Based on the results obtained in the factorial design described in Example 1 and the aim of approaching or reaching almost a 100% w/w release after 20 min, three realistic estimates of values for the process parameters were calculated. The values of the process parameters are described in Table 2 below. The composition and manufacturing process were identical to trial 1 given in Example 1.

TABLE 2

| Trial (Batch No.) | Nozzle | Spray pressure (bar) | Reaction time (min.*) | Amount of medium (g) | Chopper Yes/No | Release 20 min. (%) | Cellulose, microcryst (quality) |
|---|---|---|---|---|---|---|---|
| 1 (15089734) | 2-component | 2.2 | 16 | 1440 | No | 97.63 | Ming Tai |
| 2 (15089736) | 2-component | 0.5 | 2 | 1925 | No | 96.06 | Ming Tai |
| 3 (15089738) | 2-component | 1.6 | 8.5 | 1320 | Yes | 93.87 | Ming Tai |
| 4 (26089732) | 2-component | 2.2 | 16 | 1440 | No | 97.20 | FMC |

*Excluding the time for distribution of water

Trials Nos. 1-3 were manufactured with cellulose, microcrystalline supplied from Ming Tai. In order to investigate whether i) the results obtained with respect to the technical properties of the composition and ii) the results obtained with respect to the release of lornoxicam from the composition were influenced by employment of a specific quality of microcrystalline cellulose, another quality from another supplier (FMC) was included in trial 4 (batch No. 26089732). Trial 4 was identical to trial 1 in Table 2.

The technical properties of tablets obtained from trials 14 were identical to the results obtained in Example 1.

Conclusion

As shown in Table 2 a release of 98% w/w was achieved after 20 min, i.e. a significant improvement of the dissolution rates compared with those obtained in Example 1. Thus, the percentages released were approaching 100%.

Comparing the results from trial 4 (26089732 FMC) with trial 1 (15089734 Ming Tai) given in Table 2, indicate that no significant difference in release or technical properties of the compositions have been observed.

EXAMPLE 3

Investigation of the Influence of the Quality of Sodium Hydrogencarbonate Employed The labtrials described in the following were based on the employment of sodium hydrogencarbonate obtained from different suppliers.

Two identical compositions (trials corresponding to batch Nos. 23079733 and 23079735) were manufactured in order to test sodium hydrogencarbonate (mean particle size~120 µm) supplied from Kirsch. Previously, sodium hydrogencarbonate (mean particle size~105 µm) supplied from Tosho was used.

The manufacturing process parameters were identical to trial 5 described in Table 1 given in Example 1.

Dissolution Properties of the Cores

About 94% w/w for both trials (percentages dissolved after 20 min employing the dissolution method I described herein).

The technical properties were identical to those described in Example 1.

Conclusion

There is no significant difference between the release results of the 2 trials performed, i.e. the quality of sodium hydrogencarbonate employed does not seem to have any significant influence within the variations tested on the dissolution behaviour of a lornoxicam containing composition. Furthermore, the small variation with respect to mean particle size does not seem to have any important influence on the dissolution behaviour of a composition according to the invention.

EXAMPLE 4

Investigation of a Process Parameter (Application of Reaction Medium) on the Dissolution Behaviour The labtrial described in the following was based on the use of a 1-component nozzle.

In this trial (batch No. 27089732) a 1-component nozzle was used in order to apply the reaction medium. The composition and manufacturing process are identical to trial 1 in Example 1 apart from the following parameters:

Spray pressure: 3.5 bar
Reaction time: 16 min.
Amount of reaction medium: 1440 g
No use of chopper.

Dissolution Properties of the Cores

Release after 20 min was 98.3%.

The technical properties of the tablets were identical to those given in Example 1.

Conclusion

There is no significant difference in release behaviour compared with trial 4 in Example 2. Accordingly, using a 1-component nozzle in production scale should then be possible.

EXAMPLE 5

Upscaling to Production Scale Level

Production Scale Trial:

One trial (batch No. of the cores: 962620) was scaled up to production scale. The composition and manufacturing process of a batch size of 250,000 tablets are described below:

(Kg/250,000 tablets)

| I | Lornoxicam | 2.0 kg |
|---|---|---|
| II | Sodium hydrogencarbonate | 10.0 kg |
| III | Cellulose, microcrystalline PH 101 | 24.0 kg |
| IV | Calcium hydrogen phosphate anhydrous | 27.6 kg |
| V | L-HPC | 12.0 kg |
| VI | Hydroxy propyl cellulose | 4.0 kg |
| VII | Calcium stearate | 0.4 kg |
| VIII | Purified water | 27.0 kg |
| IX | Ethanol | 9.0 kg |
| X | Filmcoat K01187 | 30.3 kg |

II-VI were admixed in a Diosna intensive mixer with impeller speed I and chopper speed I for 1 min. Then a 10 kg aliquot was taken out of the mixer. 5 kg of this sample was manually mixed with 1. A smaller part of the remaining II-VI mixture was sieved in a Quadro Comil U 20 through a 062R sieve. Then, the I-VI mixture was sieved and added to the remaining part of the II-VI mixture followed by admixture in the Diosna to the remaining II-VI mixture. The impeller speed was I and the chopper was I for 1 min.

VIII and IX were admixed and applied to the mixture by a 1-components nozzle (Delavan ¼ BNM22X) with a spray pressure of 6.2 bar and with a spraying time of about 3 min. Impeller speed I and chopper speed I. When the spraying was completed, the reaction was continued 13 min at impeller speed I and no chopper was used.

The drying was carried out in an Aeromatic fluid bed with an inlet air temperature of about 65° C. and was continued for 45 min. Then the drying process was continued with an inlet air temperature of about 80° C. When the outlet temperature was about 42° C. and RH % (over the mixture) was about 17%, the drying was terminated. The LOD of the thus obtained particulate mixture was determined to be 1.0%.

The particulate mixture obtained was sieved in a Frewitt through a 0.71 mm sieve. VII was sieved in Quadro Comil U20 through a 062R sieve and admixed to the sieved particulate mixture in Diosna mixer for 25 sec. The impeller speed was I.

The particulate mixture was compressed into tablets by use of a Beta press rotary tabletting machine supplied by Manesty. Punches: 9.5 mm. A compound cup was used.

Technical Properties of Uncoated Tablets

Humidity (LOD): 1.2-1.4%
Disintegration time: 1'45"-2 min.
Tablet hardness: 80-100 N.

Dissolution Properties of the Cores

After 20 minutes 99.25% w/w was released (dissolution method I as described herein)

The cores were coated (batch No. of the coated tablets: 962640) with a white HPMC coat (Filmcoat K01187) in an Accela Cota 150 having 3 nozzles. Spray pressure was 6 bars as measured at the control panel and the liquid flow rate was approx. 175 g/min at the start of the process and approx. 130 g/min at the end of the process. The composition of the coat is described below:

| I | Methylhydroxypropylcellulose 5 | 1.43 kg |
|---|---|---|
| II | Propyleneglycol | 0.28 kg |
| III | Titanium dioxide | 0.90 kg |
| IV | Talcum | 0.90 kg |
| V | Purified water | 26.70 kg |

Dissolution Properties of Coated Tablets

After 20 minutes 98.62% w/w was released (dissolution method I described herein) Humidity (LOD): 2.4-2.6%

Conclusion

The results obtained demonstrate that almost a 100% release and dissolution of lornoxicam from lornoxicam tablets is obtainable even in a production scale.

EXAMPLE 6

Investigation on the Influence of the Particle Size of a Particulate Composition on the Dissolution Behaviour Labtrial of tablets (particle size of the particulate composition used to prepare tablets; above or below 212 micron).

1 particulate composition batch (batch No. 08079731) was separated into two fractions, i.e. fines (mean particle size (PS)<212 micron) and coarse material (mean particle size>212 micron). Tablets based on these two fractions (batch No. 07109731 A=<212 μm and batch No. 07109731 B=>212 μm) were manufactured.

Dissolution Behaviour 20 min dissolution of tablets based on particulate composition with a PS<212 μm: 93.1%

20 min dissolution of tablets based on particulate composition with a PS>212 μm: 85.4%.

Conclusion

The particle size of the particulate composition employed in the tabletting process seems to have a significant influence on the release rate. Furthermore, a smaller mean particle size seems to have a better behaviour with respect to fast dissolution than a larger mean particle size.

EXAMPLE 7

Upscaling—Production Scale

In this trail 5 batches were prepared after the same method as described in Example 5 apart from i) the type of nozzle used for atomization of the reaction medium, ii) the amount of reaction medium and iii) the reaction time. In Example 7 a shower type to the distribution of the medium was used which do not give a real atomization. The process parameters of these trials are shown in Table 3:

TABLE 3

| Trial No. | Amount of medium G/10,000 tab. | Reaction time* | +/− chopper | Release 20 min |
|---|---|---|---|---|
| 1 (972510) | 1440 | 16 min | − | 100.4% |
| 2 (972520) | 1440 | 8 min | − | 99.1% |
| 3 (972530) | 1340 | 16 min | − | 100.2% |
| 4 (972540) | 1340 | 8 min | − | — |
| 5 (972550) | 1440 | 6 min | + | — |

*Including time for distribution of water; approx. 2 min

The technical properties were identical to the results given in Example 5.

The cores were coated as described in Example 5.

20 min Dissolution of Coated Tablets

Coated tablets of trial 1 (972560 (batch no. of the cores: 972510)): 100.4%

Coated tablets of trial 2 (972570 (batch No. of the cores: 972520)): 100.4%

Coated tablets of trial 3 (972580 (batch no. of the cores: 972530)): 99.0%

Coated tablets of trial 4 (972600 (batch No. of the cores: 972540)): 96.1%

Coated tablets of trial 5 (972590 (batch No. of the cores: 972550)): 94.1%

The above-given results demonstrate that the amount of coating liquid and the reaction time are critical (support the results from the labtrials described in Example 1). However, the method of distribution of the reaction medium to the powder does not appear to be critical in production scale.

Conclusion

A reaction time including time for distribution of water corresponding to about 8 min seems to require at least about 1440 g of reaction medium/10,000 tablets. A reaction time including the time for distribution of water corresponding to about 6 min or below will most likely not result in a batch having a release close to 100% released after 20 min.

EXAMPLE 8

Investigation on the Influence of Sodium Hydrogencarbonate and Calcium Hydrogen Phosphate on the Properties of the Final Composition Labtrials investigating the influence of the particle size of critical excipients on the dissolution and/or technical properties were based on a $2^4$ factorial design with 2 replication of the centrepoint.

The purpose of the trials was to find the effect on the technical properties of the factors and the levels listed below.

19 trials have been performed. The manufacturing process used was identical to trial 1 in Example 1, however the spray pressure was fixed at 2.2 bar, the reaction time (excluding the time for distribution of water) at 16 min and the chopper was not used.

| Factors | 1 μm | 2 μm | 3 μm | 4 μm |
|---|---|---|---|---|
| $NaHCO_3$ | 40 | 86 | 122 | 200 |
| $CaHPO_4$ | 11 | 25*, 30 | 60 | 128 |

*The batch No. of this ingredient is identical to the batch No. used in Example 1.

20 min dissolution (for batches with a satisfactory or almost satisfactory friability), particle size of $CaHPO_4$ and $NaHCO_3$ and technical properties are shown in Table 4.

TABLE 4

| Trial No. | NaHCO$_3$ μm | CaHPO$_4$ μm | Tablet Hardness | Disintegration | Friability % | Uniformity of mass (S$_{rel}$) | Release 20 min (%) |
|---|---|---|---|---|---|---|---|
| 1(18039832) | 122* | 25* | 92.7 | 6'25" | 0.26/0.31 | 1.50 | 95.5 |
| 2(19039832) | 86 | 11 | 44.1 | 5'10" | 10.4/0.31 | 1.50 | 90.5 |
| 3(23039832) | 122 | 60 | 6.9 | 1'37" | 100 | 3.29 | — |
| 4(24039832) | 122 | 30 | 73.4 | 4'41" | 0.32/0.36 | 2.75 | 90.4 |
| 5(25039832) | 200 | 128 | 48.2 | 4'10" | 6.64/3.42 | 1.53 | — |
| 6(25039834) | 200 | 11 | 42.1 | 4'22" | 6.67/9.07 | 3.14 | — |
| 7(25039837) | 86 | 30 | 92.5 | 5'42" | 0.20/0.19 | 2.31 | 89.7 |
| 8(27039832) | 40 | 11 | 48.3 | 4'57" | 58.91/29.31 | 2.57 | — |
| 9(30039832) | 200 | 30 | 90.1 | 4'13" | 0.39/0.40 | 2.59 | 91.0 |
| 10(31039833) | 122 | 30 | 89.4 | 4'57" | 0.32/0.38 | 2.92 | 89.6 |
| 11(02049832) | 122 | 11 | 35 | 3'34" | 100 | 2.80 | — |
| 12(03049832) | 40 | 30 | 77.3 | 4'54" | 0.39/0.37 | 2.60 | 90.9 |
| 13(06049832) | 40 | 128 | 24.8 | 3'06" | 100 | 2.92 | — |
| 14(07049832) | 200 | 60 | 17.7 | 1'28" | 100 | 4.04 | — |
| 15(08049832) | 122 | 128 | 20.1 | 2'34" | 100 | 3.27 | — |
| 16(14049832) | 122 | 30 | 78.2 | 4'10" | 0.29/0.32 | 2.16 | 89.8 |
| 17(14049834) | 40 | 60 | 6.3 | 1'28" | 100 | 0.69 | — |
| 18(15049832) | 86 | 60 | 3.5 | 1'22" | 100 | 2.11 | — |
| 19(17049832) | 86 | 128 | 28.3 | 2'28" | 100 | 1.93 | — |

*The batch No. of this ingredient is identical to the batch No. used in Example 1.

Anova variance analysis with respect to crushing strength and disintegration is given in the following:

Analysis of Variance—Crushing Strength—Type III Sums of Squares

| Source | Sum of Squares | Df | Mean Square | F-Ratio | P-Value |
|---|---|---|---|---|---|
| Main Effects | | | | | |
| A: CaHPO4 | 16613.9 | 4 | 4153.48 | 83.43 | 0.0000 |
| B: NaHCO3 | 448.545 | 3 | 149.515 | 3.00 | 0.0767 |
| Residual | 547.601 | 11 | 49.7819 | | |
| TOTAL (corrected) | 18128.2 | 18 | | | |

All F-ratios are based on residual mean square error.

Figure 2:
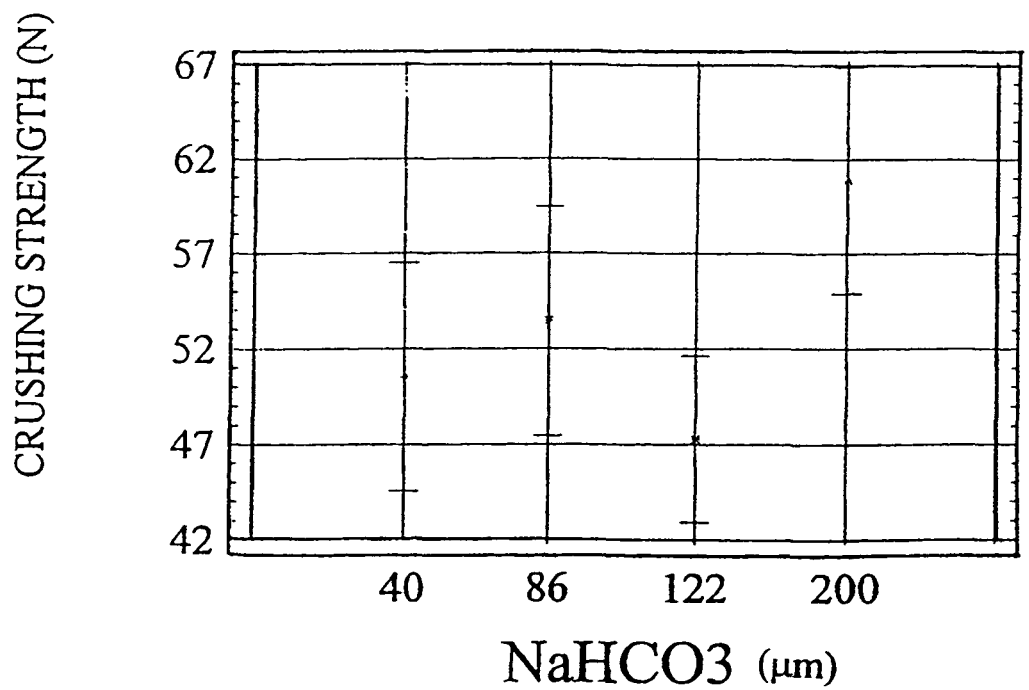
FIG. 2 is a graph of experimental data described in Example 8 indicating that the particle size of sodium hydrogencarbonate has little or no influence on the crushing strength of the tablets.

The results given above are shown in FIGS. 1 and 2 and show that the particle size of the calcium hydrogen phosphate employed has a significant influence on the crushing strength of the tablets. The particle size of the sodium hydrogencarbonate employed seems to have little or no influence on the crushing strength of the tablets.

Analysis of Variance—Disintegration—Type III Sums of Squares

| Source | Sum of Squares | Df | Mean Square | F-Ratio | P-Value |
|---|---|---|---|---|---|
| Main Effects | | | | | |
| A: CaHPO4 | 138086.0 | 4 | 34521.5 | 25.97 | 0.0000 |
| B: NaHCO3 | 3303.57 | 3 | 1101.19 | 0.83 | 0.5055 |
| Residual | 14623.8 | 11 | 1329.43 | | |
| TOTAL (corrected) | 155165.0 | 18 | | | |

All F-ratios are based on residual mean square error.

Figure 3:
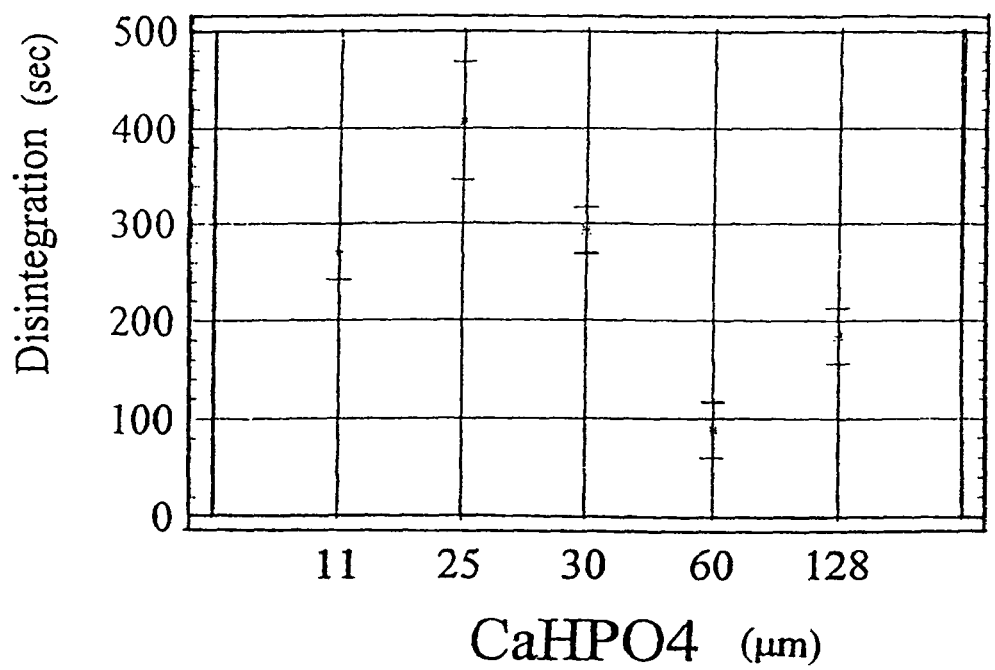
FIG. 3 is a graph of experimental data described in Example 8 indicating that the particle size of the calcium hydrogen phosphate has a significant influence on the disintegration time of the tablets.

The results given above are shown in FIG. 3 and show that the particle size of the calcium hydrogen phosphate employed has a significant influence on the disintegration time of the tablets whereas the particle size of the sodium hydrogencarbonate employed seems to have a much less pronounced influence on the disintegration time of the tablets.

Conclusion

The particle size of CaHPO$_4$ appears to have a significant effect on the technical properties (friability and disintegration time). CaHPO$_4$ having a mean particle size of approx. 11 μm, 60 μm and 128 μm does not give hard tablets but tablets with a friability % for most of them close to 100. However, the particle size of NaHCO$_3$ does not appear have a significant effect on the technical properties.

EXAMPLE 9

Water-Based Reaction 3 labtrials involving a reaction medium consisting solely of water were performed. The composition and manufacturing process were identical to the trials relating to the particle size in accordance with Example 8. The results of these trials are shown in Table 5.

TABLE 5

| Trial No. | Amount of medium (g) | Amount through a 0.18 mm sieve (%) | Tablet Hardness N | Uniformity of mass ($S_{rel}$) | Disintegration | Release 20 min. |
|---|---|---|---|---|---|---|
| 1 (20049832) | 1440 | 92 | 98.6 | 2.70 | 5'01" | 95.8 |
| 2 (22049832) | 1940 | 60.2 | 98.8 | 2.30 | 8'08" | 65.8 |
| 3 (23049832) | 1440 | 91.2 | 96.9 | 2.97 | 5'08" | 91.3 |

Conclusion

Trials 1 and 3 employing an amount of medium of 1440 g/10,000 tablets gave a release of about 91-95% w/w (dissolution method I as described herein). A higher amount of the medium (trial 2) gave a low release of 65.8% w/w and a longer disintegration time. The mean particle size of the particulate composition of trial 2 is larger than that of trial 1 and 3.

EXAMPLE 10

Upscaling—Production Scale 2 trials (batch Nos. of the cores: 020590 and 020600) were prepared in production scale. The composition and manufacturing process of the cores were identical to trial 2 in Table 3 (Example 7) (scale-up 2).

The aim of this series of batches was to improve the coating process in order to minimise the water content in the tablets after the coating (too high a water content may lead to degradation of lornoxicam).

A change in the coating process was carried out by increasing the product temperature during the coating with about 10° C., by lowering the liquid flow rate to about 80 g/min and by introducing a 1 h drying after the coating has been applied.

Technical Properties of the Cores

| Batch No.: | 020590 | 020600 |
|---|---|---|
| Humidity (LOD): | 1.33% | 1.39% |
| Disintegration: | 2-4 min | 2-3 min |
| Tablet hardness: | 90-120 N | 90-120 N |

20 min Dissolution of the Cores

020590: 97.3%

020600: 97.9%

20 min Dissolution of Coated Tablets 021170 (batch No. of the cores: 020590): 97.6%

020640 (batch No. of the cores: 020600): 96.8%

Humidity (LOD): 1.3-1.5%

Conclusion

The water content of the tablets has been reduced from about 2.0 or more to values below 1.5%.

The small increase in the disintegration time was due to an increase in the tablet hardness of approx. 20 N.

EXAMPLE 11

Production Scale Trial with Water Based Reaction

One batch (No. 020560) based on a reaction medium consisting solely of water was prepared in production scale. The composition and manufacturing process of the cores were identical to the trials in Example 10 apart from the reaction medium, which in this example was purified water The reaction time (including time for distribution of the water; approx. 2 min) was 16 min.

Tablets were compressed as described in Example 10.

Technical Properties of Cores

| Humidity (LOD): | 1.4% |
|---|---|
| Disintegration time (min): | 1'30" |
| Tablet hardness: | 50-70 N |

20 min Dissolution of the Cores

The coating process was carried out with identical process parameters as described in Example 10.

20 min Dissolution of Coated Tablets 020610 (batch No. of the cores: 020560): 91% w/w Humidity (LOD): 1.3%

Conclusion

A water-based reaction (in this case without any other solvent than water) in production scale gave a low tablet hardness. The hardness of the tablets gave some problems during the coating process. The release after 20 min seems to be lower compared to the results obtained in Example 10.

EXAMPLE 12

Investigation on the Influence of the Conjugate Reaction Conditions on the Chemical Degradation of Lornoxicam The purpose of the present example was to investigate whether the reaction between an active drug substance (lornoxicam) and an alkaline substance (sodium hydrogencarbonate) suitable can be performed before any addition of other ingredients and pharmaceutically acceptable excipients without influencing the favourable stability characteristics with respect to chemical degradation of lornoxicam.

One batch (a) of tablets having the composition listed in Example 1 was manufactured as described in Example 1 using a spray pressure of 1.3 bar, a reaction time of 9 min, an impeller and chopper speed I and with an amount of reaction medium of 1440 g. The cores were film coated using the film described in the following:

| | |
|---|---|
| Pharmacoat 603 (HPMC) | 108 g |
| Macrogol 6000 | 9 g |
| Titanium dioxide | 41 g |
| Talc | 8 g |
| Purified water | 374 g |
| Ethanol | 655 g |

The thus coated tablets were packed in double aluminium blister packages.

A second batch (b) of tablets having the composition listed below was manufactured in the following manner:

8 g of sodium hydrogencarbonate was dissolved in 120 g of water and mixed with a suspension of 32 g lornoxicam in 600 g of ethanol. While forming gaseous carbon dioxide, lomoxicam dissolved. 100 g of Pharmacoat 606W was added and dissolved. 212 g of sodium hydrogen carbonate was admixed and dissolved. The solution obtained was mixed with Avicel in a lab size mixer. The wet mixture was dried and then magnesium stearate and polyplasdone XL were admixed in the lab scale mixer.

| | |
|---|---|
| Lornoxicam | 32 g |
| Sodium hydrogencarbonate | 220 g |
| Avicel PH 101 | 998 g |
| Pharmacoat 606W | 100 g |
| Aerosil 200 | 12 g |
| Magnesium stearate | 4 g |
| Polyplasdone XL | 34 g |

The tablets were coated with the film coating shown in the table above. The amount of dry matter applied was adjusted to the number of tablets produced The coated tablets were packed in sealed glass containers.

The two batches (a and b)—which both were packed in water tight packages—were exposed to room temperature for 6 month with an intermediate measurement after 3 months. In the following are given the results (degradation product HN 33144 is a degradation product of lornoxicam):

| | Degradation product HN 33144 % w/w of total weight | | Total amount of degradation product % w/w of total weight | |
|---|---|---|---|---|
| Batch | 3 months | 6 months | 3 months | 6 months |
| a | 0.1 | 0.2 | 0.2 | 0.2 |
| b | 0.8 | 0.7 | 2.6 | 2.9 |

Conclusion

The formation of a conjugate (e.g. a sodium salt of lornoxicam) before admixing the other tabletting excipients seems to lead to a product which has a poor stability with respect to the chemical stability of lornoxicam.

EXAMPLE 13

Production Scale Investigation on the Influence of the Particle Size of Calcium Hydrogen Phosphate on the Tablet Hardness Production scale trials were carried out based on the findings in Example 8. The experiments were carried out without the addition of any therapeutically active substance.

4 trials were performed and the batches used in the trials were manufactured as described in Example 10 (batch size: 80 kg) with the only changes that calcium hydrogen phosphate was employed in qualities having a mean particle size as described below and that the therapeutically active substance, lornoxicam, was omitted from the compositions.

The mean particle sizes of the various qualities of the calcium hydrogen phosphate employed were as follows and the particle size was determined by laser light scattering:

TABLE 6

| Trial No. (Batch No.) | Mean particle size measured (n = 2), μm | Comments | Obtained tablet hardness N (n ≧ 18) |
|---|---|---|---|
| 1 (10023460) | 30 | | 101-126 |
| 2 (10023463) | 56 | | 41-62 |
| 3 (10023461) | 17 | | 96-115 |
| 4 (10023462) | 33 | Mixture 1:1 w/w of $CaHPO_4$ used in trial 2 (batch No. 10023463) and in trial 3 (batch No. 10023461) | 92-108 |

Conclusion

The hardness of the tablets obtained from trial No. 1 (batch No. 10023460) and trial No. 2 (batch No. 10023463) are in accordance with the findings in Example 8, namely that an increase in mean particle size leads to tablets having a decrease in the tablet hardness.

From Table 6 it is also seen that it is possible to obtain an acceptable tablet hardness even if the mean particle size is as low as 17 μm (trial 3). Furthermore, an acceptable tablets hardness can be obtained by use of a mixture of different qualities of calcium hydrogen phosphate having different mean particle size as long as the resulting mean particle size has a suitable size (neither too small nor too large), cf. trial 4. The latter is obtainable even though the particle size distribution changes.

EXAMPLE 14

Production Scale Continuation of Example 13 Including Incorporation of Lornoxicam in the Compositions The results of Example 13 showed that both the approx. 30 μm $CaHPO_4$ quality and the mixture of different $CaHPO_4$ qualities having a resulting mean particle size of approx. 30 μm will lead to tablets with acceptable hardness. However, the tablets prepared in Example 13 were without any therapeutically active substance. Therefore, it was tested whether the same conclusion is valid for tablets containing a therapeutically active substance such as, e.g., lornoxicam.

The following batches were produced in the same manner as described in Example 10:

1. Batch No. 10025279 containing the same type of $CaHPO_4$ as in batch No. 10023460 of Example 13.
2. Batch No. 10025280 containing the same type of $CaHPO_4$ as in batch No. 10023460 of Example 13.
3. Batch No. 10025281 containing the same type of $CaHPO_4$ as in batch No. 10023462 of Example 13.
4. Batch No. 10025282 containing the same type of $CaHPO_4$ as in batch No. 10023462 of Example 13.

The following results were obtained:

TABLE 7

| Trial No. (Batch No.) | Tablet hardness; Uncoated tablets N | 20 min. dissolution data coated tablets | | |
|---|---|---|---|---|
| | | Mean (%) | s | n |
| 1(10025279) | 81-113 | 87.2 | 1.7 | 6 |
| 2(10025280) | 86-128 | 89.9 | 0.8 | 6 |
| 3(10025281) | 68-97 | 85.8 | 1.1 | 6 |
| | | 85.4 | 1.4 | 6 |
| 4(10025282) | 87-110 | 87.5 | 0.5 | 6 | s = standard deviation
n = number of tests

Conclusion

The hardness of the tablets from the above listed batches is satisfactory for all batches. This means that mixing of $CaHPO_4$ batches with different particle sizes is possible as long as the mean particle size is close to the acceptable level of approx. 30 μm. Furthermore, incorporation of lornoxicam in the compositions does not seem to have any practical influence on the tablet hardness.

EXAMPLE 15

Labscale Trials—Effect of Reducing Particle Size of the Powder Mixture after Treatment with an Aqueous Medium In labscale tablet cores were manufactured as described in Example 8 with the exception that the batch size was 4.48 kg (in Example 8 the batch size was 3.2 kg). The composition of the individual tablets was identical to the composition given in Example 1. The batches were prepared using the following ingredients and amounts:

| I | Lornoxicam | 112.0 g |
|---|---|---|
| II | Sodium bicarbonate | 560.0 g |
| III | Avicel PH 101 | 1344.0 g |
| IV | Calcium hydrogen phosphate anhydrous | 1546.0 g |
| V | L-HPC | 672.0 g |
| VI | Hydroxy propyl cellulose | 224.0 g |
| VII | Purified water | 1512.0 g |
| VIII | Ethanol 99.9% | 504.0 g |
| IX | Calcium stearate | 5.0 g* |

*amount adjusted for a total of 1 kilogram of I-VI, i.e. the content of calcium stearate is 5.0 g/kg.

The following results were obtained:

TABLE 8

| Trial No. (Batch No.) | PS reduction method# | PS obtained* % (w/w) | Dissolution 20 min. dissolution data | | | Comments |
|---|---|---|---|---|---|---|
| | | | Mean | s | n | |
| 1 (16039832) | Dry sieving; 0.7 mm | 54 | 82.3 | 0.2 | 6 | |
| 2 (17039832) | Dry sieving; 0.6 mm | 71 | 87.8 | 0.2 | 6 | Same granulate as in trial 1 (batch No. 16039832) |
| 3 (03039932) | Wet sieving; 0.6 mm Dry sieving; 0.7 mm | 66 | 83.6 | 0.7 | 3 | |
| 4 (03039931) | Semiwet sieving; 0.6 mm Dry sieving; 0.7 | 62 | 83.7 | 0.6 | 3 | |
| 5 (12039932) | Comill; semidry; 0.27 mm Dry sieving; 0.7 mm | 97 | 91.2 | 0.7 | 3 | Rather time consuming |
| 6 (28059931) | Use of chopper at high speed during all of the wet massing phase | 70 | 89.9 | 1.1 | 6 | |

Particle Size (PS) reduction method applied during or after the granulation or drying of the particulate material (dry sieving means that the reduction method is applied after drying of the wet particulate material; wet sieving means that the reduction method is applied while the particulate material is wet and before any drying; semiwet drying means that the particulate material has almost been dried before the reduction method is applied).
*% through sieve 180 μm Conclusion All particle reduction methods seem to be suitable. The comill method, however, seems to be most efficient but it is also the most time consuming.

In accordance with Example 1 the attempt in trial No. 6 (batch No. 28059931) to avoid the formation of agglomerates by vigorous use of the chopper did only moderately improve the process as agglomerates are still present and the dissolution is still fairly low.

EXAMPLE 16

Labscale Trials—Effect of Introducing Non-Continuous Wet-Massing

In lab scale tablet cores were manufactured as described in Example 15 with the exception that the wet massing phase has been varied. The following batches were manufactured:

TABLE 9

| Trial No. (batch No.) | Wet massing time* min. | Wet massing interruption* min. | 20 min. dissolution # mean | s | n | % w/w through sieve 180 μm |
|---|---|---|---|---|---|---|
| 1 (12939933) | 1 + 1 + 1 + 1 | 3 + 3 + 3 + 3 | 97.1 | 0.6 | 3 | 72 |
| | | | 95.3 | 1.3 | 3 | |
| | | | 96.5 | 1.3 | 3 | |
| | | | 98.0 | 3.7¤ | 3 | |
| | | | 96.5 | 3.4¤ | 3 | |
| | | | 96.5 | 0.8¤ | 3 | |
| | | | 96.2 | 0.9¤ | 3 | |
| | | | 97.2 | 1.4 | 3 | |
| | | | 99.1 | 1.4 | 3 | |
| 2 (16039935) | 1 + 1 + 1 + 1 | 3 + 3 + 3 + 3 | 95.3 | 0.4 | 3 | 71 |
| | | | 96.4 | 1.4 | 3 | |
| 3 (16039936) | 1 + 1 + 1 + 1 | 3 + 3 + 3 + 3 | 93.0 | 3.5 | 3 | 70 |
| | | | 94.5 | 0.8 | 3 | |
| 4 (23039935) | 1 + 1 | 6 | 81.0 | 1.1 | 3 | 66 |
| | | | 86.9 | 1.7 | 6 | |
| | | | 85.4 | 2.1 | 6 | |
| 5 (23039936) | 1 + 1 | 30 | 93.4 | 0.4 | 3 | 67 |
| | | | 96.7 | 0.8 | 3 | |
| | | | 96.7 | 0.6¤ | 3 | |
| | | | 94.8 | 2.4¤ | 3 | |
| | | | 96.5 | 2.1¤ | 3 | |
| | | | 95.4 | 1.4¤ | 3 | |
| 6 (26039932) | 2 + 2 + 2 + 2 | 2 + 2 + 2 + 2 | 92.7 | 1.4 | 6 | 80 |
| | | | 93.5 | 0.2 | 3 | |
| 7 (26039931) | 2 + 2 + 2 + 2$ | 2 + 2 + 2 + 2 | 89.3 | 1.6 | 6 | 75 |
| | | | 91.6 | 0.7 | 3 | |
| 8 (12049940) | 1 + 1 + 1 | 15 + 15 | 97.6 | 1.8 | 6 | 69 |
| | | | 97.2 | 1.5 | 6 | |
| | | | 94.9 | 1.2 | 3 | |

*the "wet massing time" and "wet massing interruption" are to be understood in the following way. Wet massing time: 1 + 1 + 1 + 1 and wet massing interruption 3 + 3 + 3 + 3 means that the granulat has been produced by the following method: 1 min wet massing followed by 3 min interruption followed by 1 min wet massing followed by 3 min interruption and so on.

When more than one mean value is shown, the analysis have been repeated on tablets from the same trial No.

¤ The data have not been corrected for variation in tablet mass $Rpm of impeller only half the value of the other experiments. Actual value used in trial 26039931: approx. 140 rpm.

Conclusion

As can be seen from the above listed data then the introduction of periods of no agitation during the wet massing phase gives dissolution data that clearly are above what could be achieved by milling the dry granulate as described in Example 15.

However the use of periods of no agitation must be adjusted neither to have too much nor too little agitation, i.e. energy input. As an example, in trial No 4 (batch No. 23039935) it is clear that a too short overall wet massing has been employed (the dissolution results are fairly low), whereas in trial No. 7 (batch No. 26039931) too much agitation might have been used. Therefore the dissolution data for trials Nos. 4 and 7 are not as high as those obtained from trial No. 1 (batch No. 12039933).

EXAMPLE 17

Labscale Trials to Test the Set-Up in Example 16 but Employing a Smaller Batch Size Lab scale batches were manufactured as in Example 16 with the exception that the batch size has been lowered to 3.2 kg in order to test the influence of the batch size. This batch size of 3.2 kg gives the exact same composition as in Example 8. In fact batch Nos. 18039832, 24039832, 31039833 and 14049832 are from Example 8 and are quoted here again to facilitate a comparison of the data.

The following results were obtained:

TABLE 10

| Trial No. (batch No.) | Wet massing time* min. | Wet massing interruption* min. | 20 min. dissolution# mean | s | n | % w/w through sieve 180 μm after drying |
|---|---|---|---|---|---|---|
| 1 (18039832) | 16 | 0 | 95.5 | 0.5 | 6 | |
| 2 (24039832) | 16 | 0 | 90.4 | 0.6 | 6 | |
| 3 (31039833) | 16 | 0 | 89.6 | 0.8 | 6 | |
| 4 (14049832) | 16 | 0 | 89.8 | 1.1 | 6 | |
| 5 (29049932) | 1 + 1 + 1 | 15 + 15 | 95.4 | 2.2 | 6 | 68 |
| | | | 94.3 | 1.8 | 3 | |
| | | | 93.6 | 0.2 | 3 | |
| 6 (28049931) | 1 + 1 + 1 + 1 | 3 + 3 + 3 + 3 | 98.4 | 1.3 | 6 | 63 |
| | | | 98 | 1.6 | 3 | |
| | | | 9.,9 | 0.7 | 3 | |

*the "wet massing time" and "wet massing interruption" are to be understood in the following way. Wet massing time: 1 + 1 + 1 + 1 and wet massing interruption 3 + 3 + 3 + 3 means that the granulate has been produced by the following method: 1 min wet massing followed by 3 min interruption followed by 1 min wet massing followed by 3 min interruption and so on.
When more than one mean value is shown analysis have been repeated on tablets from the same trial No.

Conclusion

The conclusion from Example 16 is also valid for the trial of Example 17 even though the batch size in Example 17 is lower. There is a marked benefit with respect to the obtained dissolution results in using the interval wet massing set up described above.

Furthermore it is interesting to note that of all of the batches from Examples 16 and 17 with different interruptions of the wet massing phase no batch has a very fine particle size. This indicates that the particle size of the particulate material is not the only parameter to influence the dissolution rate.

EXAMPLE 18

Lab Scale Trials with Ibuprofen as the Therapeutically Active Substance

In lab scale, 3 types of tablet cores were manufactured. The first type (batch No. 10059932) was manufactured as described in Example 8 with the exception that lornoxicam has been substituted with ibuprofen. Therefore, the composition was as follows:

| I | Ibuprofen | 80.0 g |
|---|---|---|
| II | Sodium bicarbonate | 400.0 g |
| III | Avicel PH 101 | 960.0 g |
| IV | Calcium hydrogen phosphate anhydrous | 1104.0 g |
| V | L-HPC | 480.0 g |
| VI | Hydroxy propyl cellulose | 160.0 g |
| VII | Purified water | 1080.0 g |
| VIII | Ethanol 99.9% | 360.0 g |
| IX | Calcium stearate | 5.0 g/kg* |

*amount adjusted for a total of 1 kilo of I-VI.

The same way of manufacturing but excluding the wet massing phase, that is manufacturing the tablets by direct compression, was used for the second type (batch No. 07069934) of tablet cores.

The third type (batch No. 07069933) of tablets was manufactured in the same manner as the second type, that is by direct compression, with the exception that the sodium hydrogencarbonate was omitted.

The following results were for each dissolution test based on the measurement on 15 tablets with a declared amount of Ibuprofen of 120 mg. The dissolution method used is the following:

Test Method

Apparatus: Ph. Eur. Dissolution test for solid dosage forms and USP XXIII <711> apparatus 2, equipped with Sotax AT7. The measurements were performed using an Perkin-Elmer spectrophotometer Lambda 15.

Glass fibre filter Whatmann GFIF

Dissolution medium: 900 ml dissolution medium. (see below)

Number of revolutions: 50 rpm.

Temperature of dissolution medium: 37° C.±0.5° C.

Measuring times: At 10, 20, 30 and 60 min. (and 180 min.)

Detection UV: 221 nm

Preparation of Reagents:

Dissolution medium: Weigh out 50.0 g of sodium chloride and measure out 141.6 ml of concentrated hydrochloric acid. Dissolve the chemicals in distilled water and dilute to 25 l with distilled water.

Standards:

Stock solutions: 2 stock solutions ($S_1$ and $S_2$) with a concentration of 1000 μg/ml Ibuprofen was prepared. Ibuprofen was dissolved in dissolution medium.

Standard: Each of the stock solutions was diluted to two standards with dissolution medium: E.g. 2.00 ml was diluted to 50.00 ml and 3.00 ml was diluted to 50.00 ml, or 2.00 ml was diluted to 50.00 ml and 4.00 ml was diluted to 50.00 ml with dissolution medium.

Test Procedure 900 ml of dissolution medium is filled to each of the vessels (typically three or six vessels for the product). The medium is heated to 37° C.±0.5° C. The product to be tested (e.g. therapeutically and/or prophylactically active substance, a particulate composition, a granulate, granules or a composition in the form of a tablet, capsules or a sachet) is placed in the vessel.

A samples volume of e.g. 10 ml is extracted and filtered at the defined times. Samples and standards were diluted with ethanol to a suitable concentration (e.g. a 25 times dilution) before measuring.

Calculation for the Dissolution Method

Percentage dissolved was calculated with reference to a standard of Ibuprofen.

20 Calculate the quantity ($y_{10}$, $y_{20}$, $y_{30}$ and $y_{60}$) of Ibuprofen dissolved in per cent of the stated content in each of the tablets using the following expressions.

10 min.
$$y_1 = \frac{abs_{sample} \cdot StA}{abs_{std}} \cdot \frac{n \cdot 900 \cdot 100}{100 \cdot x}$$

20 min.
$$z_{20} = \frac{abs_{sample} \cdot StA}{abs_{std}} \cdot \frac{n \cdot (900 - v) \cdot 100}{100 \cdot x}$$
$$y_{20} = z_{20} + y_{10} \cdot \frac{v}{900}$$

30 min.
$$z_{30} = \frac{abs_{sample} \cdot StA}{abs_{std}} \cdot \frac{n \cdot (900 - 2v) \cdot 100}{100 \cdot x}$$
$$y_{30} = z_{30} + y_{10} \cdot \frac{v}{900} + y_{20} \cdot \frac{v}{900 - v}$$

60 min.
$$z_{60} = \frac{abs_{sample} \cdot StA}{abs_{std}} \cdot \frac{n \cdot (900 - 3v) \cdot 100}{100 \cdot x}$$
$$y_{60} = z_{60} + y_{10} \cdot \frac{v}{900} + y_{20} \cdot \frac{v}{900 - v} + y_{30} \cdot \frac{v}{900 - 2v}$$

Where stA=Concentration of the standard in mg/ml.

$Abs_{sample}$=Absorption of the sample $Abs_{std}$=Absorption of the standard n=Potency of the standard in percent v=sample amount in ml x=stated content The results obtained are the following:

| Time | Batch No. 10059932 n = 2 | | Batch No. 10059932 n = 3 | | Batch No. 07069934 n = 2 | | Batch No. 07069933 n = 2 | |
|---|---|---|---|---|---|---|---|---|
| | x | s | x | s | x | s | x | S |
| 10 min | 63.0 | 5.8 | 64.5 | 4.4 | 39.6 | 1.8 | 22.8 | 0.6 |
| 20 min | 65.1 | 6.7 | 62.6 | 1.2 | 43.6 | 0.6 | 26.7 | 1.3 |
| 30 min | 61.3 | 0.4 | 62.4 | 1.4 | 43.4 | 1.8 | 28.7 | 1.0 |
| 60 min | 56.2 | 2.7 | 60.2 | 0.8 | 40.2 | 0.6 | 30.4 | 0.1 |
| 180 | | | 43.2 | 6.1 | | | | |

Conclusion

From the data shown above it is evident that the first formulation type, that is the approach of Example 1, markedly improves the dissolution rate compared to a direct compression, irrespective of whether $NaHCO_3$ is present. However, the addition of $NaHCO_3$ in a direct compression has some effect on the dissolution rate.

EXAMPLE 19

Lab Scale Trials with Furosemid as the Therapeutically Active Substance

In lab scale, 3 types of tablet cores were manufactured. The first type (batch No. 06059932) was manufactured as described in Example 8 with the exception that lornoxicam has been substituted with furosemid. Therefore, the composition was as follows:

| I | Furosemid | 80.0 g |
|---|---|---|
| II | Sodium bicarbonate | 400.0 g |
| III | Avicel PH 101 | 960.0 g |
| IV | Calcium hydrogen phosphate anhydrous | 1104.0 g |
| V | L-HPC | 480.0 g |
| VI | Hydroxy propyl cellulose | 160.0 g |
| VII | Purified water | 1080.0 g |
| VIII | Ethanol 99.9% | 360.0 g |
| IX | Calcium stearate | 5.0 g/kg* |

*amount adjusted for a total of 1 kilo of I-VI

The same way of manufacturing but excluding the wet massing phase, that is manufacturing the tablets by direct compression, was used for the second type (batch No. 04069934) of tablet cores.

The third type (batch No. 04069932) of tablets was manufactured as the second type, that is by direct compression, with the exception that sodium hydrogencarbonate was omitted.

The results given below are results for each dissolution test performed and based on a measurement on 1 tablet with a declared amount of furosemid of 8 mg. The dissolution method used is dissolution method 1, only are the revolutions of the paddle changed to 50 rpm and the wavelength used is 274 nm. The substance used for standard is furosemide, the concentrations being identical to that of lornoxicam.

The following results were obtained:

| Time | Batch No. 06059932 n = 2 | | Batch No. 04069934 n = 2 | | Batch No. 04069932 n = 2 | |
|---|---|---|---|---|---|---|
| | x | s | x | s | x | s |
| 10 min | 102.4 | 1.4 | 90.2 | 2.6 | 73.8 | 0.2 |
| 20 min | 104.7 | 1.8 | 92.3 | 0.3 | 86.0 | 1.4 |
| 30 min | 104.5 | 1.0 | 93.9 | 0.9 | 93.1 | 0.7 |
| 60 min | 105.1 | 1.2 | 96.7 | 0.1 | 102.2 | 0.7 |
| 80 min | 104.3 | 1.2 | 97.3 | 0.3 | 105.1 | 0.6 |
| 100 min | 104.3 | 1.3 | 97.5 | 0.1 | 106.8 | 0.4 |

If these data are adjusted so that the end release after 100 min equals 100% the following data is obtained:

| Time | Batch No. 06059932 n = 2 | | Batch No. 04069934 n = 2 | | Batch No. 04069932 n = 2 | |
|---|---|---|---|---|---|---|
| | Org | Adj. | Org | Adj. | Org | Adj. |
| 10 min | 102.4 | 98.2 | 90.2 | 92.5 | 73.8 | 69.1 |
| 20 min | 104.7 | 100.4 | 92.3 | 94.7 | 86 | 80.5 |
| 30 min | 104.5 | 100.2 | 93.9 | 96.3 | 93.1 | 87.2 |

-continued

| Time | Batch No. 06059932 n = 2 | | Batch No. 04069934 n = 2 | | Batch No. 04069932 n = 2 | |
|---|---|---|---|---|---|---|
| | Org | Adj. | Org | Adj. | Org | Adj. |
| 60 min | 105.1 | 100.9 | 96.7 | 99.2 | 102.2 | 95.7 |
| 80 min | 104.3 | 100.0 | 97.3 | 99.8 | 105.1 | 98.4 |
| 100 min | 104.3 | 100.0 | 97.5 | 100.0 | 106.8 | 100.0 |

Org: = original data
Adj: = adjusted data

Conclusion

From the data given above it is seen that the initial release after 10 and 20 min is markedly influenced by the kind of formulation. This means that the addition of $NaHCO_3$ gives a markedly quicker dissolution rate. The formulation of type 1 seems to be the most effective indicating that the wet massing step is advantageous.

EXAMPLE 20

Lab Scale Trials—Investigation on the Influence on the Dissolution Rate by Adding Sodium Lauryl Sulphate to Lomoxicam Containing Compositions In lab scale the effect of sodium lauryl sulfate was investigated by
a) granulating with a formulation in which $NaHCO_3$ has been substituted by sodium lauryl sulfate or
b) direct compression of the formulation of Example 8 with the addition of sodium lauryl sulphate.

The actual formulation of trial a) and b) are shown below:

| | Trial a; batch No. 18069932 {gram} | Trial b; batch No. 17069932 {gram} |
|---|---|---|
| Lornoxicam | 80 | 80 |
| Sodium bicarbonate | — | 400 |
| Sodium lauryl sulphate | 32 | 32 |
| Avicel PH 101 | 960 | 960 |
| Calcium hydrogen phosphate anhydrous | 1104 | 1104 |
| L-HPC | 480 | 480 |
| Hydroxy propyl cellulose | 160 | 160 |
| Purified water | 955.5 | — |
| Ethanol 99.9% | 318.5 | — |
| Calcium stearate | 5 g/kg* | 5 g/kg* |

*adjusted for 1 kg of participate material

The composition of trial a was manufactured as described in Example 8) and the composition of trial b was manufactured by direct compression (i.e. omitting the wet massing phase).

The results obtained were the following:

| Time [min] | Trial a, batch No. 17069932 n = 3 | | Trial b, batch No 18069932 n = 3 | |
|---|---|---|---|---|
| | x | s | x | s |
| 10 | 25.1 | 1.1 | 23.0 | 0.5 |
| 20 | 28.2 | 0.6 | 28.0 | 0.2 |
| 60 | 30.9 | 0.5 | 32.2 | 0.1 |
| 120 | 32.0 | 0.6 | 33.9 | 0.1 |

Conclusion

From the results given above it is seen that the addition of a surface active agent like sodium lauryl sulphate does not lead to a quick release of lornoxicam. The same result is seen in the case where sodium hydrogencarbonate as well as sodium lauryl sulphate are present in the composition.

The invention claimed is:

1. A quick release pharmaceutical composition for oral administration comprising lornoxicam or a pharmaceutically acceptable salt, complex or prodrug thereof,
   the composition being in the form of a particulate composition or being based on a particulate composition, wherein either the particles of the particulate composition used in the manufacture of the composition have a mean particle size of at the most 250 micrometers, or
   at least 50% w/w of the particles of the particulate composition used in the manufacture of the composition pass through a 180 micrometer sieve;
   wherein the quick release pharmaceutical composition contains the lornoxicam in contact with an alkaline substance in a ratio of one part lornoxicam to up to five parts alkaline substance; and
   the composition, when tested in accordance with the dissolution method I defined herein employing 0.07 N hydrochloric acid as dissolution medium, releases at least 80% w/w of the lornoxicam within the first 20 minutes of the test.

2. A composition according to claim 1, further comprising at least one pharmaceutically acceptable excipient.

3. A composition according to claim 2, wherein the at least one pharmaceutically acceptable excipient is selected from the group consisting of binders, disintegrants, fillers and diluents.

4. A composition according to claim 3, wherein the composition comprises a filler having binding properties.

5. A composition according to claim 4, wherein the filler having binding properties is selected from the group consisting of lactose, sugar derivatives, calcium carbonate ($CaCO_3$), tricalcium phosphate ($Ca_3(PO_4)_2$), calcium hydrogen phosphate ($CaHPO_4$) and/or mixtures thereof.

6. A composition according to claim 4, wherein the filler having binding properties is calcium hydrogen phosphate.

7. A composition according to claim 4, wherein the filler having binding properties as raw material has a mean particle size of at the most 140 μm.

8. A composition according to claim 1, comprising a further active drug substance.

9. A composition according to claim 1, wherein the further active drug substance is an antidepressant, an opioid, a prostaglandine analogue, a glucocorticosteroid, a cytostaticum, a $H_2$ receptor antagonist, a proton pump inhibitor and/or an antacidum.

10. A composition according to claim 8, wherein the further active drug substance is misoprostol, methotrexate, cimetidine, ranitidine, pantoprazole, omeprazole, lansoprazole, paracetamol, penicillamine, sulfasalazine and/or auranorfin.

11. A composition according to claim 1, in unit dosage form, wherein the unit dosage of the composition comprises from 1 to 32 mg of lornoxicam.

12. A composition according to claim 1, in unit dosage form, wherein the unit dosage comprises from 1 mg to 1.6 g of lornoxicam.

13. A composition according to claim 1, wherein the unit dosage of the composition contains 1, 2, 3, 4, 8, 12, 16, 20, 24, 28, 32 or 36 mg of lornoxicam.

14. A composition according to claim 1, wherein the water content in the composition is at the most 5% w/w determined by the LOD (loss on drying) method described herein.

15. A composition according to claim 1, comprising sodium hydrogen carbonate.

16. A composition according to claim 1, comprising calcium hydrogen phosphate.

17. A composition according to claim 1, wherein the alkaline substance is an antacid or an antacid-like substance.

18. A composition according to claim 1, wherein the quick release pharmaceutical composition is a coated tablet.

19. The composition of claim 1, comprising lornoxicam, sodium hydrogen carbonate, microcrystalline cellulose, calcium hydrogen phosphate anhydrous, L-HPC, hydroxy propyl cellulose, water, ethanol, and calcium stearate.

20. The composition of claim 1, comprising lornoxicam, sodium hydrogen carbonate, microcrystalline cellulose, calcium hydrogen phosphate anhydrous, L-HPC, hydroxy propyl cellulose, and calcium stearate.

21. The composition of claim 1, wherein the composition has a mechanical strength to enable the composition to be coated using traditional coating equipment.

22. The composition of claim 1, further comprising a filler having binding properties, wherein the composition comprising the binder in the form of tablets having a diameter of 9.5 mm when subjected to a crushing strength test in accordance with Ph. Eur. has a crushing strength of at least about 50N.

23. The composition of claim 1, wherein the particles of the particulate composition comprises a granulate.

24. A composition according to claim 17, wherein the alkaline substance is an antacid or an antacid-like substance selected from the group consisting of sodium hydrogen carbonate, magnesium carbonate, magnesium hydroxide and magnesium metasilicate aluminate or mixtures thereof.

25. A composition according to claim 24, wherein the mean particle size of the antacid-like substance as raw material is at the most 250 μm.

* * * * *